United States Patent
Burger-Kentischer et al.

(10) Patent No.: US 10,613,105 B2
(45) Date of Patent: Apr. 7, 2020

(54) COMPETITIVE IMMUNOASSAY TEST SYSTEM FOR DETECTING A PYROGEN

(71) Applicant: FRAUNHOFER-GESELLSCHAFT ZUR FORDERUNG DER ANGEWANDTEN FORSCHUNG E.V., Munich (DE)

(72) Inventors: Anke Burger-Kentischer, Stuttgart (DE); Steffen Rupp, Stuttgart (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 901 days.

(21) Appl. No.: 14/941,891

(22) Filed: Nov. 16, 2015

(65) Prior Publication Data
US 2016/0327580 A1 Nov. 10, 2016

(30) Foreign Application Priority Data
Nov. 17, 2014 (DE) .................. 10 2014 223 430

(51) Int. Cl.
*G01N 33/92* (2006.01)
*G01N 33/558* (2006.01)
(Continued)

(52) U.S. Cl.
CPC ....... *G01N 33/92* (2013.01); *G01N 33/54386* (2013.01); *G01N 33/558* (2013.01);
(Continued)

(58) Field of Classification Search
CPC ............ G01N 33/92; G01N 33/54386; G01N 33/558; G01N 33/56916; G01N 2400/50;
(Continued)

(56) References Cited

U.S. PATENT DOCUMENTS 5,573,921 A * 11/1996 Behnke ............ G01N 33/54366
422/401
6,908,742 B2 * 6/2005 Neely .............. G01N 33/56916
435/7.21
(Continued)

FOREIGN PATENT DOCUMENTS

CN 103308686 A 9/2013
CN 1033088686 * 9/2013 ........... G01N 33/545
(Continued)

OTHER PUBLICATIONS

European Search Report regarding Application No. EP15194954.2, dated Apr. 4, 2016. Machine translation provided.

*Primary Examiner* — Gailene Gabel
(74) *Attorney, Agent, or Firm* — Stephen T. Olson; Harness, Dickey & Pierce, P.L.C.

(57) ABSTRACT

The invention relates to a competitive immunoassay test system as well as a method to simply and rapidly detect pyrogens contained in a sample by means of the pyrogen binding domain of pattern recognition receptors. The test system comprises an assay carrier having at least one immobilized pyrogen binding domain of a pattern recognition receptor with a labeled, displaceable ligand, wherein the displacement of the ligand is indicated by a pyrogen contained in the sample by a color reaction of the labeling. The assay carrier preferably also has at least one immobilized ligand capture protein, which binds the displaced ligand and thereby initiates a color reaction of the labeling.

20 Claims, 10 Drawing Sheets
Specification includes a Sequence Listing.

(51) Int. Cl.
*G01N 33/569* (2006.01)
*G01N 33/543* (2006.01)

(52) U.S. Cl.
CPC ... *G01N 33/56916* (2013.01); *G01N 2400/50* (2013.01); *G01N 2469/10* (2013.01); *G01N 2800/26* (2013.01); *G01N 2800/709* (2013.01)

(58) Field of Classification Search
CPC ........... G01N 2469/10; G01N 2800/26; G01N 2800/709
See application file for complete search history.

(56) References Cited

U.S. PATENT DOCUMENTS

| | | | |
|---|---|---|---|
| 2005/0208470 A1 | 9/2005 | Latz et al. | |
| 2008/0248508 A1* | 10/2008 | Baker | C08B 37/0003 435/7.92 |
| 2010/0129836 A1 | 5/2010 | Goodnow | |

FOREIGN PATENT DOCUMENTS

| | | |
|---|---|---|
| DE | 42 29 591 C1 | 3/1994 |
| EP | 1 327 886 A1 | 7/2003 |
| EP | 1715341 A1 | 10/2006 |
| GB | 2 204 398 A | 11/1988 |
| WO | 97/44665 A1 | 11/1997 |

\* cited by examiner

Capillary flow rates in sec/3 cm

SEQUENCE LISTING

```
<160> NUMBER OF SEQ ID NOS: 7

<210> SEQ ID NO 1
<211> LENGTH: 20
<212> TYPE: PRT
<213> ORGANISM: Artificial Sequence
<220> FEATURE:
<223> OTHER INFORMATION: Peptide

<400> SEQUENCE: 1

Lys Gly Glu Thr Val Asn Thr Thr Ile Ser Phe Ser Phe Lys Gly Ile
1               5                   10                  15

Lys Phe Ser Lys
            20

<210> SEQ ID NO 2
<211> LENGTH: 20
<212> TYPE: PRT
<213> ORGANISM: Artificial Sequence
<220> FEATURE:
<223> OTHER INFORMATION: Peptide

<400> SEQUENCE: 2

Lys Met Gln Tyr Pro Ile Ser Ile Asn Val Asn Pro Cys Ile Glu Leu
1               5                   10                  15

Lys Gly Ser Lys
            20

<210> SEQ ID NO 3
<211> LENGTH: 20
<212> TYPE: PRT
<213> ORGANISM: Artificial Sequence
<220> FEATURE:
<223> OTHER INFORMATION: Peptide

<400> SEQUENCE: 3

Gly Leu Leu His Ile Phe Tyr Ile Pro Arg Arg Asp Leu Lys Gln Leu
1               5                   10                  15

Tyr Phe Asn Leu
            20

<210> SEQ ID NO 4
<211> LENGTH: 20
<212> TYPE: PRT
<213> ORGANISM: Artificial Sequence
<220> FEATURE:
<223> OTHER INFORMATION: Peptide

<400> SEQUENCE: 4

Lys Arg Lys Glu Val Ile Cys Arg Gly Ser Asp Asp Tyr Ser Phe
1               5                   10                  15

Cys Arg Ala Leu
            20
```

```
<210> SEQ ID NO 5
<211> LENGTH: 10
<212> TYPE: PRT
<213> ORGANISM: Artificial Sequence
<220> FEATURE:
<223> OTHER INFORMATION: Peptide

<400> SEQUENCE: 5

Phe Met Met Leu Gly Gly Leu Val Arg Ile
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Peptide

<400> SEQUENCE: 6

Arg Met Met Trp Phe Gly Ile Met Val
1               5

<210> SEQ ID NO 7
<211> LENGTH: 22
<212> TYPE: PRT
<213> ORGANISM: Artificial Sequence
<220> FEATURE:
<223> OTHER INFORMATION: Peptide

<400> SEQUENCE: 7

Ser Gly Ser Pro Glu Glu Met Leu Phe Cys Leu Glu Phe Val Ile Leu
1               5                   10                  15

His Gln Pro Asn Ser Asn
            20
```

COMPETITIVE IMMUNOASSAY TEST SYSTEM FOR DETECTING A PYROGEN

CROSS-REFERENCE TO RELATED APPLICATIONS

This application is a continuation-in-part of German Application No. 10 2014 223 430.1 filed 17 Nov. 2014, the disclosure of which application is incorporated herein by reference.

FIELD

The invention relates to a competitive immunoassay test system as well as a method to simply and rapidly detect pyrogens contained in a sample by means of the pyrogen binding domain of pattern recognition receptors. The test system comprises an assay carrier having at least one immobilized pyrogen binding domain of a pattern recognition receptor with a labeled, displaceable ligand, wherein the displacement of the ligand is indicated by a pyrogen contained in the sample by a color reaction of the labeling. The assay carrier preferably also has at least one immobilized ligand capture protein, which binds the displaced ligand and thereby initiates a color reaction of the labeling.

BACKGROUND

Pyrogens are designated as inflammatory acting substances that can induce fever. A differentiation is made in this case between bacterial pathogens, viral pathogens, pyrogens of fungi and pyrogens of a non-biological origin, such as e.g., metal compounds in elastomers, rubber abrasion or microscopic plastic particles from medical technology products or pharmaceuticals. Among the bacterial pyrogens a differentiation is made between endotoxins from the membrane of gram-negative bacteria, such as e.g., lipopolysaccharides (LPS), and components of gram-positive bacteria, such as e.g., lipoteichoic acids.

Pyrogens that have invaded the body stimulate immune cells that are capable of phagocytosis to synthesize proinflammatory cytokines, in particular interleukins (primarily IL-1 and IL-6) and tumor necrosis factor-a (TNF-a), which then as the "actual pyrogens" influence the temperature center of the body in such a way that increased heat production and reduced heat dissipation occur. The immune system is thus stimulated and normally the invading microorganism is eliminated. However, pathogenic microbes and products thereof, i.e., pyrogens, can in some circumstances invade the bloodstream from a source of infection and thus systemically activate an inflammatory cascade, which produces a systemic inflammatory response that is no longer controlled. The clinical complex of symptoms associated with this inflammatory response is designated as sepsis or colloquially as "blood poisoning". Since 1992, four separate degrees of severity have been differentiated in this connection: systemic inflammatory response syndrome (SIRS), sepsis, severe sepsis and septic shock. Sepsis as such is defined as SIRS with a confirmed infection.

In the course of sepsis, frequently a life-threatening impairment of vital functions occurs and the failure of one or more organs (multi-organ failure). Intensive care can bridge critical phases by temporarily replacing or supporting organ functions (ventilation, renal replacement therapy, cardiovascular therapy, coagulation therapy). Despite this, sepsis must be classified as a very severe illness with an extremely serious prognosis: 30-50% of those afflicted die despite maximum treatment. The earliest possible start of treatment is crucial for survival. In Germany 150,000 people fall ill with sepsis every year; 56,300 of them die.

The prognosis is particularly unfavorable when treatment is started late, sources of infection cannot be localized, or pathogens cannot be identified. Therefore, rapid and reliable identification of the pathogens or the pathogen spectra is of great significance for initiating a targeted treatment of the infection in clinical diagnostics in hospitals.

Most of the time, pathogens that cause sepsis are bacteria, predominantly gram-negative bacteria like *E. coli*, other *enterobacteria*, species of *Klebsiella*, *Proteus* and *Enterobacter*, *Pseudomonas aeruginosa*, *Neisseria meningitides* and *Bacteroides*, but also gram-positive bacteria like *Staphylococcus aureus*, *Streptococcus pneumoniae* and other *streptococci*; rare fungi, viruses, or parasites. When the cells of the non-specific immune defense come into contact with lipopolysaccharides (LPS), i.e., components of the bacterial cell wall, peptidoglycans or lipoteichoic acids (LTA), the innate immunity is activated, and in the early phase of the infection cytokines are secreted from various immune cells. Even though these cytokines play an important role in the defensive reaction, activated neutrophils for example are attracted to the site of infection, and the entrance of these cytokines and bacterial substances into the circulatory system produces a chain of unfavorable pathophysiological events, which can lead to death via sepsis and septic shock.

The spectrum of the pyrogenic substances that occur depends on the pathogen or pathogen spectrum. Certain pathogens form pathogen-specific molecular structures or pyrogen patterns, so-called pathogen-associated microbial patterns or PAMPs, which are detected by special, so-called pattern recognition receptors (PRRs) such as toll-like receptors (TLR), NOD-like receptors (NLR), RIG-I-like receptors (RLR), C-type lectin receptors (CLR), cytosolic dsDNA sensors (CDSS), scavenger receptors, mannose-binding lectin 2 (MBL-2) receptor and glucan receptors. Among PRRs, the toll-like receptors (TLR) constitute the largest and best known family.

TLRs are highly conserved transmembrane proteins with leucine-rich extracellular domains and a cytoplasmic domain of approximately 200 amino acids. Because of their homology in the cytoplasmic domain, they belong to the interleukin-1 receptor/toll-like receptor super family. The extra cellular domain is directly involved in detecting different pathogenic molecular structures and therefore constitutes the binding domain of the receptor. TLRs are activated via the binding of PAMPs, i.e., foreign structures. As of today, ten different human TLRs have been identified. They are expressed in different cells types in the immune system, predominantly in monocytes, macrophages, dendritic cells as well as B-cells and T-cells.

TLR 2 is essential for identifying a plurality of PAMPs of gram-positive bacteria, including bacterial lipoproteins and lipoteichoic acids. TLR 3 is involved in identifying double-stranded virus RNA. TLR 4 is activated predominantly by LPS gram-negative bacteria. TLR 5 detects bacterial flagellin. TLR 7 and TLR 8 detect synthetic small antiviral molecules and single-strand RNA. TLR 9 was detected in endoplasmic reticulum (ER) and after stimulation with DNA containing CpG motives, for example CpG oligodeoxynucleotides, is recruited to endosomal/lysosomal compartments. CpG motives are areas within a nucleic-acid strand, in which the building blocks of cytosine (C) and guanine (G) unexpectedly frequently occur ("p" stands for a phosphate group, which connects the two building blocks "C" and "G"); such CpG motives are found especially frequently in the genome of bacteria and viruses, but not those of vertebrates. The specificity of TLRs is expanded by the interaction of two TLRs so that e.g., TLR 2 and TLR 1 are in a position as a heterodimeric molecule to identify triacylated lipoprotein. Dimers of TLR 2 and TLR 6 can identify diacylated lipoprotein.

With the presence of a septic illness or even already with the suspicion of such an illness, treatment must occur at an early stage. Until now, blood cultures from the patient have been used for microbiological testing for diagnosis when there is an indication of sepsis. This process costs valuable time and frequently does not identify the pathogens, because this is possible only with vital pathogens. Pyrogenic substances of the pathogens such as cell wall components cannot be determined with this method.

Currently four commercial detection systems for pyrogens have been approved in corresponding EU and FDA regulations for pyrogens: the rabbit pyrogen test (KPT), *limulus* amoebocyte lysate test (LAL), the immune pyrogen test (IPT) and the monocyte activation test (MAT).

The rabbit pyrogen test is based on the "fever reaction" of animals to pyrogens. It is an animal test, in which the test substance is applied to the rabbit's ear vein. In order to detect a defensive reaction of the animal's body to the substance, a measurement is taken of the rectal fever after several hours. This test is time-consuming and expensive and associated with the calculated suffering of animals. A further serious disadvantage of this test is the high variance in the results, caused by living and therefore individual organisms. Pyrogens can be detected with it, but they cannot be identified. A test for viruses is also not possible. In addition, transferability to humans is limited, because not all human pyrogenic substances also trigger a fever in a rabbit.

Another known test is the *limulus* amoebocyte lysate test (LAL, e.g., PyroGene from Lonza; ToxinSensor from GenScript Inc.). This test uses the fact that the haemolymph of the *Limulus polyphemus* (horseshoe crab) coagulates in the presence of LPS gram negative bacteria. This method is more sensitive and can be standardized better than the known rabbit test, but it detects only LPS gram-negative organisms (limit of detection: 3 pg/mL); other pyrogens remain undetected.

Another known test is the immune pyrogen test, e.g., Endosafe-IPT (Charles River). It is based on the "fever reaction" of human cells to the presence of pyrogens. It is a human whole blood test, in which cytokine IL-1 is secreted from vital blood cells as a response to a pyrogenic substance, which can be determined quantitatively using ELISA (limit of detection: 20-50 pg/mL). This system also detects pyrogens of gram-positive pathogens. However, the test is associated with still a greater amount of time and effort. Human whole blood must be made available, which is a potential human pathogen.

The monocyte activation test (MAT, e.g., PyroDetect System, EMD Millipore Corporation; PyroDetect Kit Biotest AG) is also based on the detection of cytokine IL-1 formed by monocytes using ELISA, wherein in comparison to IPT cryo-blood is used. It is not possible to specify the pyrogens.

In addition to the pharmacopoeia-approved tests that have been described so far, there are other in vitro methods for detecting pyrogens for use in research. These are mammalian cells, which stably express the TLRs and are able to specifically indicate the presence or absence of pyrogens with the aid of a reporter gene (e.g., HEK-blue and RAW-blue TLR cells from InvivoGen). In addition, DE 10 2006 031 483 discloses a cellular pyrogen test, wherein a transgenic NIH-3T3 cell expresses at least one TLR and a reporter gene, which is under the expression control of an NF-κB inducible promoter.

The known tests are time-consuming and require a well-equipped laboratory (ELISA test, human blood processing, animal experiments) as well as expertise in handling cell cultures. For this reason, these test systems are only suited for well-trained users, for example in research or specialized laboratories. As a result, there is a need for a test system for detecting pyrogens that can be conducted quickly and simply. Moreover, there is a need for a test system for specifying pyrogen patterns (PAMPs) in order to be able to draw conclusions from them about the pathogens or pathogen spectrum.

Furthermore, medical technology products and pharmaceuticals must be tested for the absence of pyrogens in order to prevent pyrogens from getting into the bloodstream in this manner. The absence of pyrogens is therefore a mandatory prerequisite for the use of these types of products on the body. There is a need for improved tests for pyrogenic residues on medical instruments, donor tissue, injectable drugs and medical products such as implants or instruments (catheters, etc.) There is also a need in the food industry and pharmaceutical industry for the improved detection of pyrogenic substances and microbes and the identification thereof in foodstuffs, food ingredients, raw materials, and starting materials for foodstuffs or drugs.

SUMMARY

Therefore, the technical problem underlying the present invention is, above all, overcoming the aforementioned disadvantages and in particular making available a means and method for the simple and rapid, but specific, detection and identification of pyrogens in a sample.

The technical problem is addressed by making available a competitive immunoassay test system for detecting at least one pyrogen contained in a liquid sample, comprising an assay carrier having at least one immobilized pyrogen binding domain of at least one pattern recognition receptor (PRR) with at least one labeled, displaceable ligand, wherein the displacement of the labeled ligand from the pyrogen binding domain of the PRR is indicated by the pyrogen contained in the sample by a color reaction of the labeling. In other words, the labeled, displaceable ligand and the at least one immobilized pyrogen binding domain are configured so that the color reaction takes place during displacement of the labeled ligand from the pyrogen binding domain.

Moreover, the assay carrier in a preferred embodiment can have at least one immobilized ligand capture protein for binding the displaced, labeled ligand, wherein the binding of the ligand to the ligand capture protein is indicated by a color reaction of the labeling.

The immunoassay test system according to the invention is based on a competitive immunodetection, wherein the pyrogen to be detected has a higher binding affinity for the immobilized pyrogen binding domain of the PRR than the labeled, displaceable ligand, which is initially present bound to the binding domain and is competitively displaced from the pyrogen to be detected. This means the labeled, displaceable ligand and the pyrogen to be detected are different substances. The labeled ligand and the pyrogen are at best similar substances (but not, however, the same substance), which differ only by the presence of labeling. In particular, the displaceable ligand and the pyrogen to be detected differ by their binding affinity to the immobilized pyrogen binding domain, wherein the pyrogen to be detected always has a higher binding affinity than the displaceable ligand, thereby ensuring that the pyrogen is able to displace the ligand from the pyrogen binding domain, i.e., the receptor preferably is able to completely and quantitatively displace it.

The test system according to the invention therefore makes it advantageously possible to dispense with the use of animal testing or time-consuming and costly equipment, very expensive blood tests, or cell culture processes. Furthermore, the immobilized pyrogen binding domains of individual PRRs as binding molecules for the corresponding pyrogen makes it possible to detect specific pathogens and PAMPs, which can be conducted simply and directly on site.

In a preferred embodiment, the assay carrier is a microtiter plate well, a reagent container, a test tube or a substrate capable of capillary flow. The pyrogen binding domains of the PRR(s) and preferably the ligand capture proteins are immobilized on surfaces of the respective assay carrier suitable for this purpose, such as, e.g., the base and/or wall of a microtiter plate well, a reagent container or a test tube as well as the surface of a substrate capable of capillary flow.

If the assay carrier is configured as a microtiter plate well, a reagent container or a test tube, the detection of pyrogen preferably takes place in a liquid medium, i.e., preferably an aqueous solution, in particular a suitable buffer. The detection can then occur either directly, i.e., by the color reaction initiated directly during the displacement of the labeled ligand, or indirectly, i.e., by the binding of the displaced ligand through corresponding ligand capture proteins. The displaced ligands hereby reach, via diffusion, the ligand capture proteins that are likewise immobilized on the wall and/or base of the assay carriers. Therefore, it is preferably not provided according to the invention to add the labeled, displaceable ligand required for the verification in the form of a further component or separate solution. Moreover, an inverse verification is preferably not planned in accordance with the invention, in other words, a verification of the pyrogen contained in the sample by a reduction in the dye or the color reaction. Therefore, to carry out the method according to the invention no color scales are preferably required which correlate the intensity of the dye with the pyrogen content in the sample, rather a color reaction directly indicates the presence of one or more pyrogens in the sample.

In an especially preferred embodiment of the present invention, the assay carrier is a substrate that is capable of capillary flow, which has the following areas in the direction of capillary flow each spaced apart from one another:

a) A sample application area,
b) A reaction area having the at least one immobilized pyrogen binding domain of at least one PRR with the at least one labeled, displaceable ligand and
c) An analysis area having the at least one immobilized ligand capture protein for binding the displaced labeled ligand.

In this embodiment, the test system according to the invention is based on a competitive immunochromatographic detection of the pyrogen. Because it is thereby a special embodiment of a competitive immunoassay, the conditions listed in the foregoing for a competitive immunoassay preferably apply likewise for this, provided that they are applicable to a substrate that is capable of capillary flow.

The test system according to the invention detects pyrogens in liquid samples. The liquid sample is preferably a clinical sample, a medical technology sample, a pharmaceutical sample, a food technology sample or an environmental sample. The clinical sample is especially preferably a sample of human or animal origin. In the case of an environmental sample, it is especially preferably a water sample, in particular a drinking water sample or a sample from bathing waters. Of course, the immunoassay test system according to the invention can be used to analyze all types of samples in which the presence of pyrogens is suspected as long as they are present in liquid form and in sufficient volume.

The preferred substrate capable of capillary flow according to the invention preferably comprises, in addition to the sample application area a), the reaction area b) and the analysis area c), a control compound area b'), having at least one adsorbed, labeled control compound that does not bind to the pyrogen binding domain of the PRR or the ligand capture protein and d) a control area having at least one immobilized control compound capture protein for binding the at least one labeled control compound.

A sample or solution possibly containing a pyrogen arrives at the reaction area b) via the sample application area a) through capillary flow. In the reaction area b), bound to the substrate is at least one immobilized pyrogen binding domain of at least one PRR, on which labeled, displaceable ligands are bound. The pyrogen to be detected has a higher binding affinity to the immobilized pyrogen binding domain of the PRR than the labeled, displaceable ligand. This is significant because the detection of the pyrogen is based on a competitive displacement of the labeled ligand, which then is specifically detected in the analysis area, preferably by a color reaction. Because the specific pyrogen has a higher binding affinity to the immobilized pyrogen binding domain of the PRR, the labeled ligand displaces from the pyrogen binding domain of the PRR and is carried further by capillary flow. The pyrogen is therefore detected in the analysis area indirectly by the binding of the displaced labeled ligand. The preferably present mobile, i.e., non-immobilized control compounds are likewise carried further by the capillary flow, because they are entirely absorbed on the substrate and can thus indicate whether the liquid sample has penetrated to the analysis area. The successful execution of the test can thus be controlled in order to prevent false negative results. In the analysis area, the labeled ligands displaced by the specific pyrogen through the pyrogen binding domain of the PRR are bound by specific immobilized ligand capture proteins in the analysis area and thus detected. This can preferably be indicated by a color reaction, which is first initiated by the binding of the labeled ligands to the ligand capture proteins in the analysis area. Alternatively, it is also preferably possible that the color labeling of the displaceable ligands is already visible in the reaction area, in the case of a displacement by the pyrogen contained in the sample, is transported further in the capillary flow and then concentrated by the binding to the ligand capture protein in the analysis area. The control compound is preferably bound by the control compound capture proteins and detected.

In conjunction with the present invention, the term "pyrogen" is understood as human and/or animal pathogenic bacteria, viruses, fungi and parasites as well as components thereof, molecular structures and PAMPs, but also substances of a non-biological origin, for example metal compounds in elastomers, rubber abrasion or microscopic plastic particles from medical technology products or pharmaceuticals.

According to the invention, the pyrogen to be detected is at least one selected from the group consisting of bacterial lipoproteins, bacterial lipopeptides, bacterial peptidoglycans, bacterial lipoteichoic acids, zymosan of yeast, double-stranded virus RNA, bacterial lipopolysaccharides (LPS), bacterial flagellin, unmethylated bacterial or viral DNA containing CpG, single-strand virus RNA and human heat shock protein 60.

To detect one or more of the pyrogens specified in the foregoing, the pyrogen binding domains of at least one PRR is used in the immunoassay test system according to the invention. The pyrogen binding domain of a PRR preferably comprises those areas of the respective receptor which are responsible for detecting a pyrogen, i.e., the binding thereof. Therefore, the pyrogen binding domain constitutes only a portion of the entire receptor, which is involved however in the direct detection of the pyrogens. The corresponding receptor domains can either be cut off from entire protein by corresponding enzymes, isolated from overexpressing cells, expressed in vitro via correspondingly transfected cells as a shortened protein or expressed by means of cell-free protein synthesis with the aid of the transcription and translation apparatus of lysed cells and ultimately purified.

Of course, it is also possible to immobilize the entire PRR on the assay carrier, preferably in reaction area b) of the substrate capable of capillary flow. Therefore, it can be provided according to the invention that the reaction area b) has at least one immobilized PRR with labeled, displaceable ligand.

The pyrogen binding domain of a PRR or the entire receptor protein can be expressed via correspondingly transfected cells and purified. The proteins obtained in this or another manner can be immobilized either in an undirected manner, for example via physisorption utilizing electrostatic interactions, van der Waal interactions, ionic interactions, hydrogen bridge bonds and hydrophobic interactions, or in a directed manner on the assay carrier, for example by means of affinity adsorption with the aid of so-called "tags". In this case, the corresponding tag is tied during the expression to the opposite protein terminus on the pyrogen binding domain so that during the affinity adsorption the protein terminus with the pyrogen binding domain always points away from the carrier surface. In this connection, the tags have a high binding affinity to their respective binding partner. Examples of such affinity pairings are streptavidin/avidin and biotin, maltose and maltose-binding protein (MEP), glutathione and glutathione S-transferase (GST) as well as streptavidin and histidine. The proteins can also be immobilized on the assay carrier by means of chemisorption via covalent bonds to functional side groups of amino acids such as amino-, carboxyl-, hydroxyl- and thiol groups via isourea compounds, diazo compounds, peptide bonds or alkylation reactions.

According to the invention, it can be provided that intact cells, which express the corresponding PRR(s) on the surface of the cell, or lysates of cells, which express PRRs, can be printed directly with the inkjet printing process as a complete cell or cell lysate on the assay carrier, preferably the substrate capable of capillary flow and thus be immobilized. Protein-based, in particular bio-inks with gelatin, are used for this purpose.

In a preferred embodiment of the present invention, the at least one immobilized pyrogen binding domain of the PRR is selected from the group consisting of the pyrogen binding domains of a toll-like receptor (TLR), a NOD-like receptor (NLR), a RIG-I-like receptor (RLR), a C-type lectin receptor (CLR), a cytosolic dsDNA sensor (CDSS), a scavenger receptor, a mannose-binding lectin 2 (MBL-2) receptor, a glucan receptor and combinations thereof. Especially preferably the at least one immobilized pyrogen binding domain is the pyrogen binding domain of a TLR. In a preferred embodiment, the at least one immobilized pyrogen binding domain of one or more TLRs is selected from the group consisting of TLR 1, TLR 2, TLR 3, TLR 4, TLR 5, TLR 6, TLR 7, TLR 8, TLR 9 and heterodimers thereof. Therefore, depending upon the selection or composition of the immobilized pyrogen binding domain(s) of different PRRs, in particular TLRs or heterodimers of same, various pyrogens can be specifically detected, i.e., individually or even different pyrogen groups.

In a preferred embodiment of the invention, the pyrogen binding domains of at least two different PRRs, in particular TLRs, are immobilized on the assay carrier, in particular in reaction area b) of the substrate capable of capillary flow. Correspondingly, at least two labeled, displaceable ligands are bound to the pyrogen binding domains and correspondingly at least two ligand capture proteins are provided, which are specific for respectively one ligand. The at least two ligands can be labeled with the same or different color label(s).

In this embodiment, the pyrogen binding domains of at least two different PRRs, each with labeled ligands, are preferably immobilized on the substrate capable of capillary flow in a reaction area b) and the at least two ligand capture proteins in an analysis area c). However, it can also be provided that the test system according to the invention has respectively a reaction area for the immobilized pyrogen binding domain of a PRR and respectively an analysis area for the corresponding ligand capture proteins. The same then applies to the sample application area a) and, if present, to the control compound area b') and the control area d).

In an especial preferred embodiment of the present invention, the at least one immobilized pyrogen binding domain of the PRR is the pyrogen binding domain of TLR 4. In this embodiment, the immunoassay test system according to the invention is able to detect lipopolysaccharides (LPS) contained in the sample as pyrogens from gram-negative bacteria.

In another especially preferred embodiment, of the present invention, the at least one immobilized pyrogen binding domain of the PRR is the pyrogen binding domain of TLR 9. In this embodiment, the immunoassay test system according to the invention can be used to detect unmethylated bacterial or viral DNA containing CpG that is contained in the sample.

The labeled, displaceable ligand has a lower, preferably average, binding affinity to the pyrogen binding domain of the PRR as compared to the pyrogen specific for the PRR. This ensures that the labeled ligand can be displaced from the to-be-detected pyrogen from the PRR, in particular the pyrogen binding domain of the PRR. The ligand is therefore preferably a pyrogen-like substance or compound, which though it is able to bind to the pyrogen binding domain, however with lower binding affinity than the actual pyrogen. The displaceable ligand is preferably a low-molecular weight compound, especially preferably a derivative of the substances selected from the group consisting of pyrimidine, quinoline, sulphonamide, carboxamide, phenanthroline, piperarzine, benzenesulfonamide, pyrazine, naphtyridine and morpholine; a peptide, preferably consisting of 7 to 17 amino acids; a single-strand CpG-DNA oligodeoxynucleotide; a adenine analogue; a polyinosinic:polycytidylic acid; a lipoprotein; a lipid; a muramyl-dipeptide; a hyaluronic acid fragment; a double-stranded DNA nucleotide; a carbohydrate, especially preferably a derivate of mannose or fucose; a peptidoglycan or a double-stranded RNA nucleotide. The binding affinity of the ligand can preferably be further influenced and adjusted by adjusting suitable conditions on or in the assay carrier, such as, e.g., the pH value and/or the selection and concentration of suitable buffer salts.

The displaceable ligand and, in a preferred embodiment, the control compound, are labeled, in particular color labeled. It is especially preferred that the displaceable ligand and, if present, the control compound are labeled either with the same or different color labeling(s) selected from the group consisting of fluorescence dyes, in particular fluorescein isothiocyanate (FITC), fluorescein, rhodamine, ATTO dyes, Texas Red, phycoerythrin derivatives, cyanine fluorescence dyes, tetramethylrhodamine 5-carboxamido-(6-azidohexanyl) (TAMRA), Alexa Fluor 488; colored latex particles, soot particles, magnetic particles, quantum dots, colloidal selenium particles, gold nanoparticles, gold clusters, colloidal gold particles, colloidal selenium particles; enzymes, in particular horseradish peroxidase (HRP), alkaline phosphatase (AP), glucose oxidase (GOx), β-D-galactosidase (β-Gal), glucose 6-phosphate dehydrogenase (G6PD); chemiluminescent compounds, in particular acridinium ester, acridinium sulfonamide, isoluminol; streptavidin, avidin and biotin.

The detection of the labeling always takes place label-specifically. Direct color labeling, such as fluorescence dyes or quantum dots, is measured by an increase or decrease in the fluorescence intensity with a suitable excitation wavelength. Colored particles such as latex particles, soot particles or colloidal selenium particles can be visually detected without the aid of additional analysis instruments, if they concentrated spatially based on the bond of the ligand to the ligand capture proteins. Magnetic particles can be detected by means of changes in the residual magnetism and the easing of tension in the magnetic material. Gold nanoparticles are preferably detected via surface enhanced Raman spectroscopy. Detection by means of enzymes is accomplished photometrically via the conversion of suitable colored enzyme substrates and an associated change in color or by means of changes in intensity of the chemiluminescence. Especially preferred substrates of HRP are based on chromogenic substrates such as 3,3',5,5'-tetramethylbenzidine (TMB), 3,3'-diaminobenzidine (DAB), 2,2'-azino-bis(3-ethylbenzthiazoline-6-sulfuric acid) (ABTS), o-phenylenediamine dihydrochloride (OPD) or chemiluminescent substrates such as enhanced chemiluminescence substrate (ECL). Preferred substrates of AP are based on 5-bromo-4-chloro-3-indolyl phosphate (BCIP), para-nitrophenyl phosphate (pNPP) or acridine substrates. Preferred substrates of GOx are nitro-blue tetrazolium salts and 5-bromo-4-chloro-3'-indoly phosphate. Preferred substrates of β-Gal are o-nitrophenyl β-D-galactopyranoside and 5-bromo-4-chloro-3-indolyl β-D-galactopyranoside. Preferred substrates of G6PD are 4-nitrophenyl α-D-glucopyranoside, 5-bromo-4-chloro-3-indolyl β-D-glucuronide [and] 4-nitrophenyl β-D-glucuronide. Chemiluminescent compounds are analyzed in suitable analysis devices via the change in the luminescence.

In the case of labeling with the system of streptavidin/avidin and biotin, detection occurs indirectly via a conjugation of the streptavidin or avidin with suitable enzymes such as HRP, AP or fluorescent dyes such as fluorescein or rhodamine and the analysis described in the foregoing.

The color labeling is bonded to the ligand and the control compound as the case may be using standard coupling methods that are familiar to a person skilled in the art.

In a preferred embodiment, the ligand capture proteins are specific antibodies, in particular monoclonal or polyclonal antibodies, which specifically bind the displaceable ligand. Binding the labeled ligand initiates a color reaction, which indicates the binding of the displaced ligand. In another preferred embodiment, the ligand capture proteins are monoclonal or polyclonal antibodies, which specifically bind the color labeling of the displaceable ligand.

In a preferred embodiment, the ligand capture proteins [and] also the pyrogen binding domains of the PRRs can be on the substrate capable of capillary flow. In an especially preferred embodiment, the pyrogen binding domains of the PRR(s) immobilized in the reaction area of the substrate capable of capillary flow can thus be used as the ligand capture proteins and likewise be immobilized in the analysis area. In a preferred embodiment, the ligand capture proteins can be specific antibodies and pyrogen binding domains of the PRRs.

The control compound is preferably a substance or a molecule, which has as similar a structure as possible as compared to the displaceable ligand, but does not bind to the pyrogen binding domain of the PRR. Because of the similar as possible structure of the control compound and the displaceable ligand a similar as possible run behavior of both substances in the capillary flow of the substrate is advantageously facilitated. As a result, an especially exact control of the test can take place, because the control compound and the displaceable ligand are transported approximately equally rapidly in the capillary flow and thus is can be ensured that a positive control reaction is also conclusive and, if applicable, a displaced ligand was transported to the analysis area. The control compound is preferably a substance that does not bind to the pyrogen binding domain of the PRR, for example a low molecular-weight compound, especially preferably a derivate of the substances selected from the group consisting of pyrimidine, quinoxaline, quinoline, benzene, quinazoline imidazoline, sulphonamide and carboxamide; a peptide, preferably consisting of 7 to 17 amino acids; a single-strand CpG-DNA oligodeoxynucleotide; a adenine analogue; a polyinosinic:polycytidylic acid; a lipoprotein; a lipid; a muramyl-dipeptide; a hyaluronic acid fragment; a double-stranded DNA nucleotide; a carbohydrate, especially preferably a derivate of mannose or fucose; peptidoglycan or a double-stranded RNA nucleotide.

The control compound capture proteins are preferably specific antibodies, which specifically bind the control compound. Because the control compound is labeled, in particular color labeled, a color reaction is initiated by the binding of the control compound to the control compound capture proteins and the bond is made visible. In another preferred embodiment, the control compound capture proteins are monoclonal or polyclonal antibodies, which specifically bind the color labeling of the control compound.

In a preferred embodiment, the areas a), b) and c) on the substrate capable of capillary flow are each spaced apart from each other. In a preferred embodiment, the different areas do not overlap, but have a distance between each other or are adjacent to one another.

In a preferred embodiment, the substrate capable of capillary flow has areas a), b), b'), c) and d). The areas a), b), c) and d) are then preferably spaced apart from one another and the area b) and b') can be spaced apart from each other or preferably overlap each other. In this embodiment, the areas a), b), c) and d) thus have a distance between each other or are adjacent to one another and the areas b) and b') have a distance between each other, are adjacent to one another or overlap each other. The areas b) and b') preferably completely overlap one another. In a preferred embodiment, the areas b) and b') constitute one area so that the immobilized pyrogen binding domain of at least one of a pattern recognition receptor with the labeled, displaceable ligand as well as the adsorbed labeled control compounds are located in one and the same area of the substrate capable of capillary flow.

Moreover, the different areas are preferably arranged in the following sequence on the substrate capable of capillary flow: a), b) and c) or a), b), b') and d), wherein the areas b) and b') can overlap, in particular completely overlap, or be present separate from one another.

In a preferred embodiment, the immunoassay test system according to the invention has a substrate capable of capillary flow as an assay carrier, preferably consisting of a substrate capable of capillary flow, which has the areas a), b), c) and preferably b') and d). Substrate is understood in conjunction with the present invention as a fixed matrix, in particular a carrier matrix, which can receive liquid samples and permits a capillary flow of the sample, in particular of substances contained in the sample, such as, e.g., pyrogens, and is furthermore suitable for immobilizing receptor proteins, antibodies or even cells or cell lysates. The substrate can optionally be present in a supported manner, i.e., be stabilized by a more solid material, specifically the carrier. The substrate itself can preferably be round, oval, square or in the form of a strip, i.e., be designed in the form of a circle, oval, square or a strip. The substrate is especially preferably designed in the form of a strip, i.e., rectangular. The individual areas are preferably arranged thereon in succession, preferably along the longitudinal axis of the rectangle.

The substrate capable of capillary flow is especially preferably a porous substrate of nitrocellulose, cellulose acetate, charge-modified nylon, polyethersulfone, polyvinylidene fluoride, glass-fiber membranes, sol-gel coatings of aluminum oxide, titanium dioxide, silicon dioxide or similar materials or combinations thereof. If the substrate consists of a combination of different materials, said materials may preferably abut each other, merge into each other or overlap each other. The substrates are preferably selected from Table 1 below.

The immunoassay test system according to the invention thus preferably comprises as an assay carrier a substrate capable of capillary flow or combinations of several substrates capable of capillary flow, the assay carrier preferably consists of the substrate(s) capable of capillary flow. However, it can also be provided according to the invention that the substrate capable of capillary flow is contained in a device, for example a housing, which facilitates handling. The device preferably has recesses, which permit for example the application of the sample on the sample application area and the reading out of the analysis area and, if present, the control area.

The present invention relates further to a method for detecting at least one pyrogen contained in a liquid sample, preferably comprising the following process steps:
 i) Making available a test system,
 ii) Bringing a liquid sample into contact with the assay carrier and
 iii) Analyzing the color reaction.

If the assay carrier of the test system according to the invention is a microtiter plate well, a reagent container or a test tube, the "bringing into contact" of the liquid sample with the assay carrier is understood as introducing the sample to the reaction vessel, i.e., the microtiter plate well, the reagent container or the test tube.

According to the invention, by introducing the liquid sample into the microtiter plate well, the reagent container or the test tube, a pyrogen contained in the sample can diffuse to the immobilized pyrogen binding domains of the PRR and displace the labeled ligand from the binding domain. A color reaction of the labeling is initiated either directly by the displacement or the displaced ligand is indirectly bound by likewise immobilized ligand capture proteins, thereby initiating a color reaction of the labeling.

In a preferred embodiment of the method according to the invention, the assay carrier is a substrate capable of capillary flow and the liquid sample is applied to the sample application area a) in step ii) or the sample application area of the substrate is immersed in the sample. In the process, conditions are provided and maintained, which produce a capillary flow in the substrate of the sample application area a) to the analysis area c), preferably to the control area d).

The conditions that produce a capillary flow in the substrate are preferably maintained for a time period of at least one minute, in particular one minute to 24 hours, in particular 10 minutes to 12 hours, in particular 15 minutes to 1 hour, preferably 20 minutes to three hours, preferably 30 minutes to two hours.

According to the invention, by applying the liquid sample to a substrate capable of capillary flow, a pyrogen contained in the sample is transported by capillary flow in the direction of the reaction area b), binds there to the immobilized pyrogen binding domain of the PRR and thereby displaces the labeled ligand from the immobilized pyrogen binding domain of the PRR, which is transported further to the analysis area c), bound there by the immobilized ligand capture protein and detected.

A control compound adsorbed in the control compound area b') is preferably transported by the capillary flow to the control area d), bound there by the immobilized control compound capture protein and detected.

All terms used in the present description, such as e.g., pyrogen binding domain, pattern recognition receptor (PRR or TLR), displaceable ligand, ligand capture protein, control compound and control compound capture protein, also comprise the plurality of corresponding components.

Additional preferred embodiments of the present invention can be found in the dependent claims.

The present invention will be explained in greater detail based on an example and the following figures.

BRIEF DESCRIPTION OF THE DRAWINGS

The figures show:

FIG. 10A dried overnight at 37° C.; FIG. 10B fixed with 70% ethanol; FIG. 10C stored for 96 hours at 4° C.

DETAILED DESCRIPTION

Example 1: Verification of LPS Through TLR4

1.1 Material Selection

Pyrogens, bacteria, and the residues thereof are found all around us in our everyday lives and in production processes and can be inactivated only by dry heat greater than 180° C. As a result, the absolute freedom from pyrogens of all material used is essential (individual components of the immunoassay test system, solutions, buffers, substrates, consumable materials for laboratories, laboratory equipment). This is necessary, because pyrogens have a naturally high affinity for TLR4, i.e., the pyrogen binding domain, which is used here as a sensor element, bind thereto and therefore adversely affect or completely prevent the functionality of the immunoassay test system.

All components of the immunoassay test system, such as substrates, blocking solutions, etc., were rigorously tested for their freedom from pyrogens using an established PAMP assay (DE 10 2006 031 483; EP 2 041 172). For this assay, the TLR4 receptor complex was stably transfected and expressed in a NIH 3T3 fibroblast cell line and a secreted alkaline phosphatase (SEAP) was stably integrated as the reporter gene. The activation of TLR4 by pyrogens leads to the activation of the transcription factor NF-κB, which is turn induces the SEAP expression. Pyrogens, which are located in or on potential components of the immunoassay test system, can thus be detected by the expression of the reporter gene and then only pyrogen-free components can be selected for the structure of the immunoassay test system.

Figure 1:
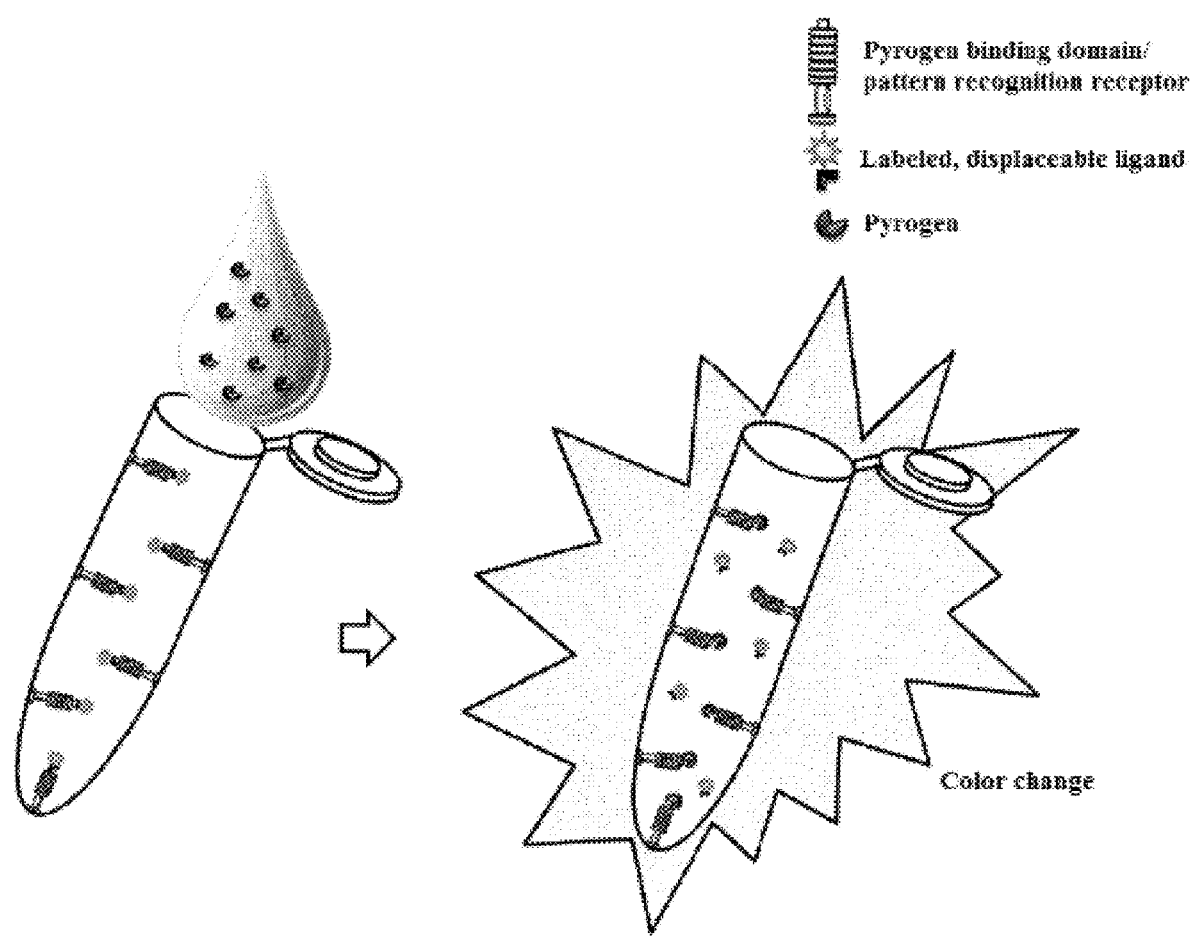
FIG. 1 shows the immunoassay test system according to the invention, wherein the assay carrier is designed as a test tube and pyrogen binding domains of a pattern recognition receptor (PRR) are immobilized on the inner surface of the test tube.
Figure 2:
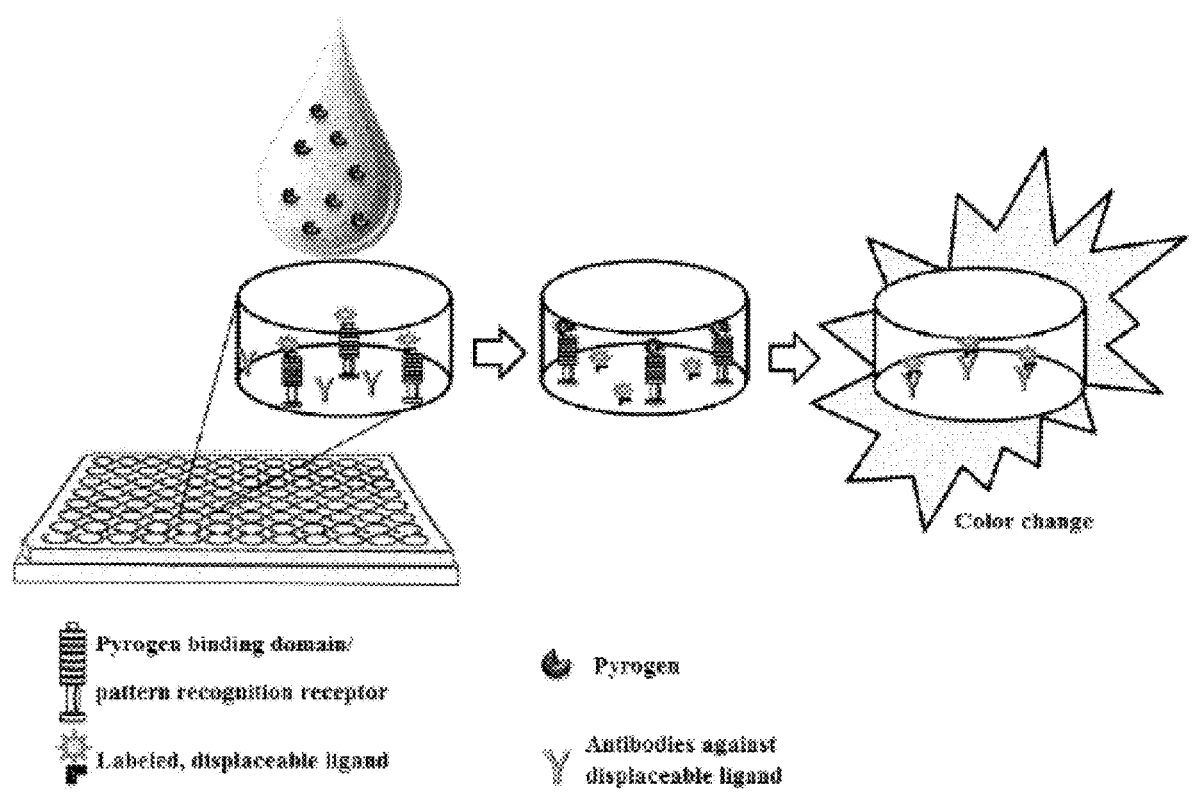
FIG. 2 shows the immunoassay test system according to the invention, wherein the assay carrier is configured as a microtiter plate well and pyrogen binding domains of a PRR and ligand capture proteins (antibodies) are immobilized on the base of the well.
Figure 3:
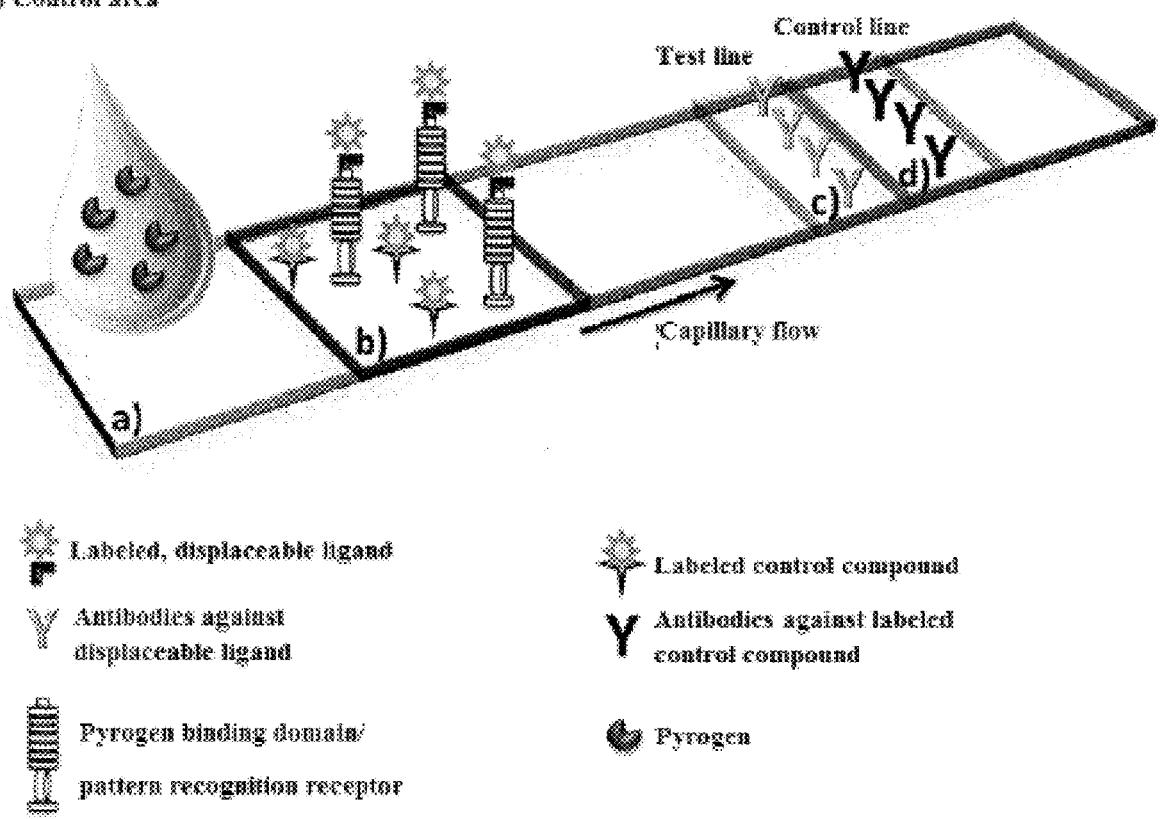
FIG. 3 shows the immunoassay test system according to the invention, wherein the assay carrier is configured as a substrate capable of capillary flow and pyrogen binding domains of a PRR are immobilized in the reaction area b) and a labeled control compound is absorbed and a sample containing a pyrogen is applied to the sample application area.
Figure 4:
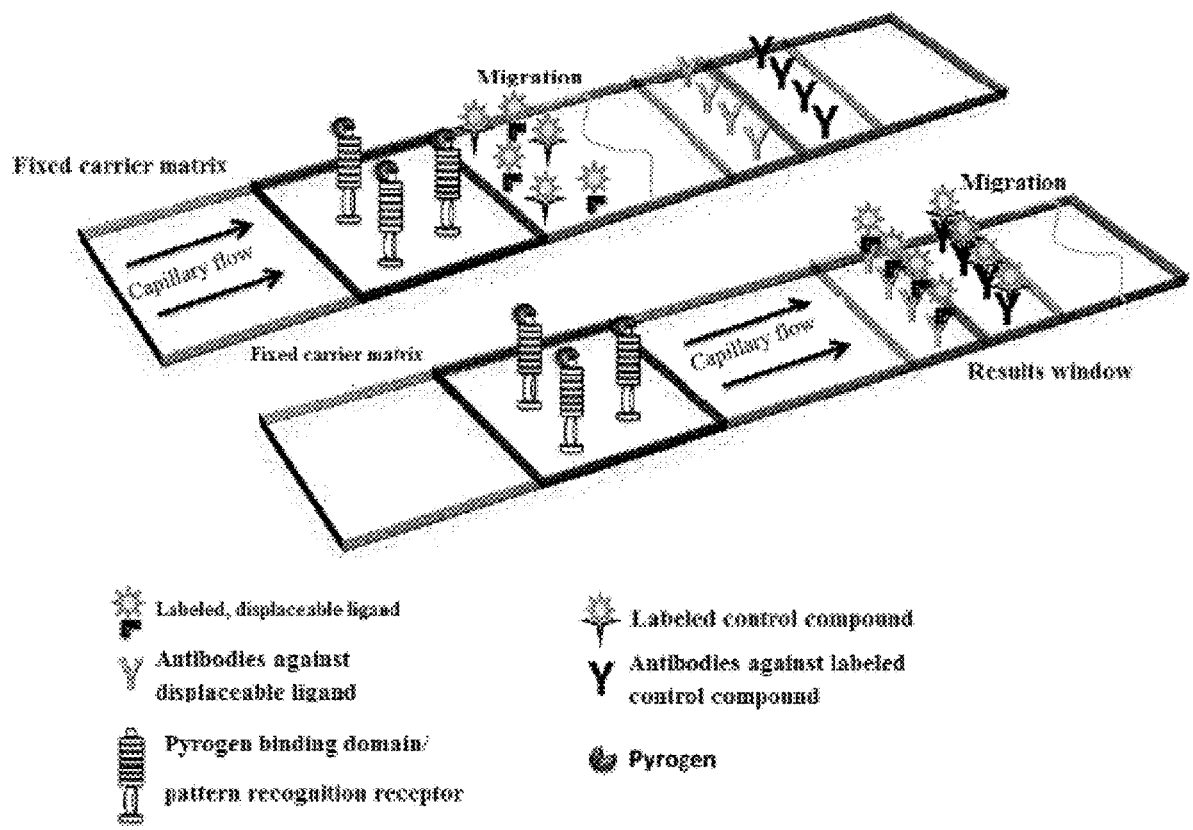
FIG. 4 shows the displacement of the labeled ligand from the pyrogen binding domain by the pyrogen. At the same time, the adsorbed control compound is carried along by the capillary flow. In the results window, the labeled ligand is bound by the ligand capture proteins (antibodies) and the labeled control compound by the control compound capture proteins (antibodies) and thus detected.
Figure 5:
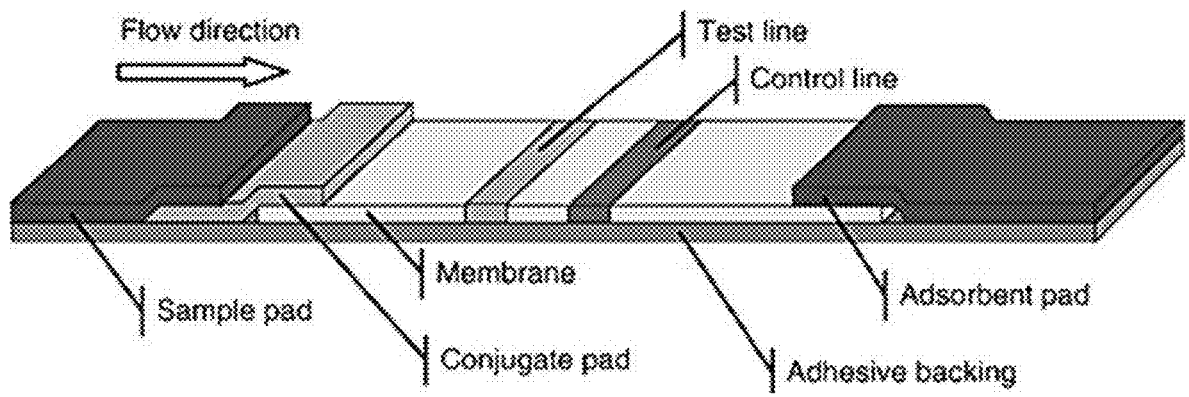
FIG. 5 shows another possible schematic structure of an assay carrier according to the invention.

FIG. 5 shows an example of the possible structure of an assay carrier according to the invention, which is configured as a substrate that is capable of capillary flow.

The assay carrier of a test strip according to the invention, i.e., the substrate that is capable of capillary flow in the present case, is normally composed of a composite of several materials, each of which individually assumes a specific task. FIG. 5 schematically shows such a structure of a sample pad, conjugate pad, membrane and adsorbent pad.

The sample to be analyzed is applied in the area of the sample pad, i.e., the sample application area. On the one hand, this guarantees a uniform and homogeneous sample transport and, on the other hand, can be used to retain particles. TLR4 pyrogen bind domains are immobilized on the overlapping conjugate pad, i.e., the reaction area. This can take place directly on the material or with the aid of particles such as agarose beads, which are kept here on site. In addition, the conjugate pad can contain buffer chemicals, blocking reactions or stabilizers. The separation between the control compound and the displaceable TLR4 ligand as the detection molecule takes place via the membrane. Both molecule types are captured at the end thereof via ligand capture proteins or control compound capture proteins in order to display the test result. The adsorbent pad (adsorbent material) at the end of the test strip absorbs excess liquid and guarantees the necessary capillary flow in the test strip.

TABLE 1

Compilation of materials investigated for the substrate

| | | Function | |
|---|---|---|---|
| | Designation | Source of Supply | Technical Data |
| Sample pad | CF3 | GE Healthcare | Sample and Adsorption pad, cotton linters, 322 μm thickness |

TABLE 1-continued

Compilation of materials investigated for the substrate

| Function | Designation | Source of Supply | Technical Data |
|---|---|---|---|
| Sample pad/ Adsorbent pad | CFSP203000 | Merck Millipore | Cellulose, 83 µm thickness, can be used as both a sample pad and an adsorbent pad |
| Conjugate release pad | Standard 14 | GE Healthcare | Glass fiber, 355 µm thickness |
| Conjugate release pad | GFCP103000 | Merck Millipore | Glass fiber, 48 µm thickness |
| Membrane | FF120HP | GE Healthcare | Nitrocellulose membrane (100 µm), with plastic back (100 µm), flow rate: 90-150 s/4 cm |
| Membrane | FF170HP | GE Healthcare | Nitrocellulose membrane (100 µm), low viscosity, with plastic back (100 µm), flow rate: 140-200 s/4 cm |
| Membrane | Immunopore SP | GE Healthcare | Nitrocellulose membrane (100 µm), with plastic back (100 µm), flow rate: 190-280 s/4 cm |
| Membrane | Immunopore FP | GE Healthcare | Nitrocellulose membrane (100 µm), with plastic back (100 µm), flow rate: 140-200 s/4 cm |
| Membrane | Millipore High Flow Plus | Merck Millipore | Nitrocellulose |
| Membrane | Protran BA85 | Whatman | Nitrocellulose, pore size: 0.45 µm |
| Adsorbent pad | CF3 | GE Healthcare | Sample and adsorption pad, cotton linters, 322 µm thickness |
| Adsorbent pad | CF5 | GE Healthcare | Absorption pad, cotton linters, 954 µm thickness |
| Special material | Fusion 5 | GE Healthcare | Glass fiber with plastic back portion, material that simultaneously assumes all of the aforementioned functions |

Figure 6:
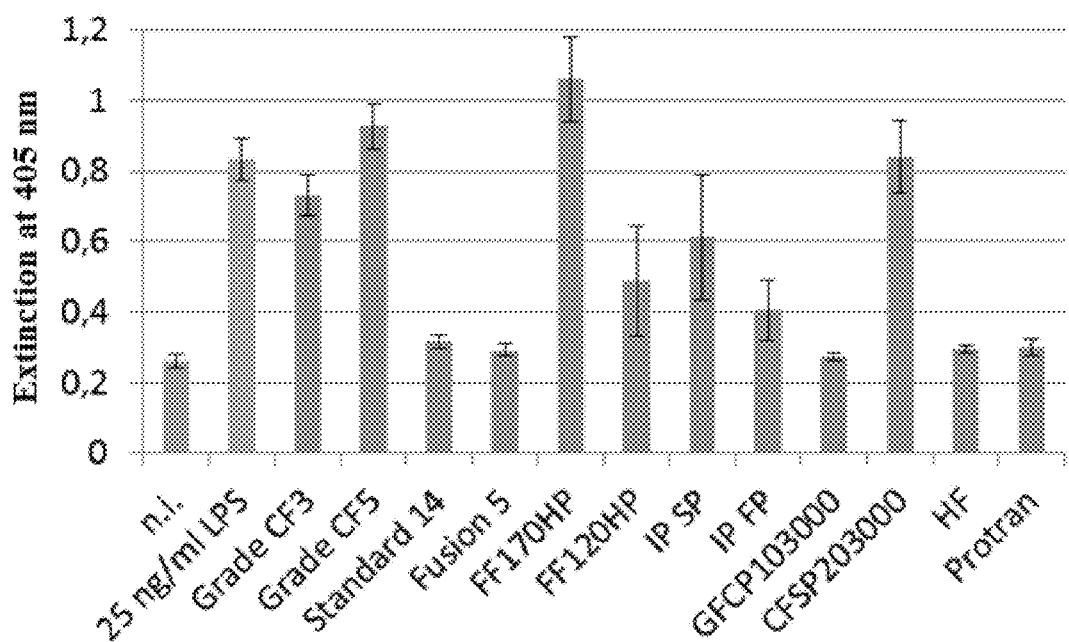
FIG. 6 shows the results of a PAMP assay, which was performed with the NIH 3T3 pNifty SEAP TLR4/CD14 reporter cell line. 25 ng/mL of LPS served as a positive control, and n.i. is the non-induced negative control. The substrate turnover (p-nitrophenyl phosphate) of the SEAP formed in the supernatant was analyzed photometrically after 60 min with a wavelength of l=405 nm.

The tested substrates (see Table 1) were ordered from GE Healthcare, Merck, Millipore and Whatman. However, all of them are not produced under sterile conditions, which could be shown in the material eluates tested in the PAMP assay (FIG. 6). The CF3, CF5 and CFSP203000 adsorbent pads in particular showed a very strong activation of the TLR4 receptors and thus a pyrogen contamination. Nevertheless, it is possible to use these materials for the structure of the test strip, because they do not come into direct contact with the reaction area on the opposite end of the test strip. Only the use of the CFSP203000 material as a sample pad and the use of the FF170 HP membrane were dispensed with. No activation of TLR4 could be detected for the materials of the most sensitive reaction area, the conjugate pad. Therefore, the tested materials are substantially suitable for the structure of the immunoassay test system according to the invention.

Figure 7:
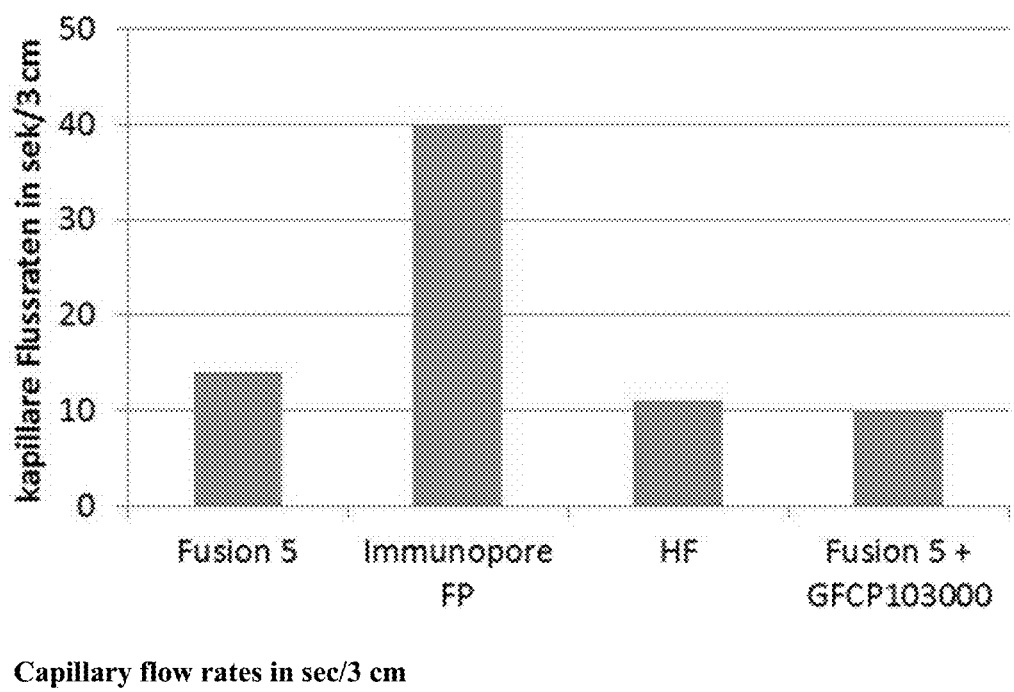
FIG. 7 shows the flow rates of the membranes in the test strip structure with 300 μL of sample solution. Structure of the test strip (width 2 cm): Standard 14 as the sample pad (1 cm length), various membranes (5 cm length) and CF3 as the adsorbent pad. It shows the flow rates of the following membranes: Fusion 5, Immunopore FP, HF as well as Fusion 5+Conjugate Pad GFCP10300 (1 cm length). 300 μL of a Ponceau S solution was applied to the sample pad as the sample solution.

An important parameter of the immunoassay test system is the flow rate of the liquid front in the test strip, because it determines the contact time with the pyrogen binding domain of the TLR4 receptor and thus the time that is available for displacement of the color-labeled, displaceable ligand via LPS. Therefore, to further characterize the substrates, a test strip with a width of 2 cm was structured as an example according to the diagram in FIG. 5. All test strips consisted of Standard 14 as a sample pad (1 cm length) and CF3 as an adsorbent pad (2 cm length). The flow rate of the Fusion 5, Immunopore FP, HF and Fusion 5+Conjugate Pad GFCP10300 (1 cm length) membranes, in each case with a length of 5 cm, were analyzed as follows: Different volumes (100/200/300/400/500 µL) of a Ponceau S solution were applied to the sample pad. The uniformity of the migration, the absorbency of the materials and therefore the minimum required volume of the sample, as well as the time that the migration requires to reach a defined migration length of 3 cm were assessed. FIG. 7 presents the flow rates of the different membranes when applying 300 µL of Ponceau solution.

The Immunopore FP membrane clearly sets itself apart from the other 3 tested membranes, because it is hardly absorbent and has the highest flow rate of 40 sec/3 cm with a uniform migration. The Fusion 5 material in particular is a very absorbent material, which can easily absorb up to 500 µL with greater sample volumes, however, it is not functional with sample volumes that are too low. By additionally combining the Fusion 5 with a conjugate pad (GFCP103000), absorbency is increased further and the flow rate drops to 10 sec/3 cm. Thus, various materials are available for different requirements with respect to sample volumes and test speed.

In order to avoid non-specific bonds of the labeled control compounds and ligands on the tested membranes, the unoccupied membrane binding sites must be saturated, i.e., blocked. Roti® Block (Carl Roth GmbH) showed itself to be the most suitable in terms of freedom from pyrogens, reproducibility and cytotoxic effect.

1.2 Supplying the Receptors

Isolated TLR4 receptors or the pyrogen binding domains thereof were ordered for the immunoassay test system from the following sources:

Recombinant TLR4 from NS0 cells (mouse myeloma cells), R&D Systems, 3146-TM-050/CF TLR4 protein fragment from wheat germ lysate, Abcam, ab112362

TLR4/CD284 from baculovirus insect cells, Hölzel Diagnostik GmbH, 10146-H08B-100

TLR4/CD284 (Hölzel Diagnostik GmbH) in particular was used in the following.

1.3 Fluorescent Labeling of the Displaceable Ligand and the Control Compound

To verify the displacement of the displaceable ligand and to verify the functionality of the test strip via the control compound, they must be detected after they are bound by corresponding capture proteins. Corresponding molecules are especially easy to detect by means of color labeling. The method of fluorescent labeling, the labeling with fluorophores, is advantageous here especially compared with the visual analysis of non-fluorescent dyes, because small quantities of the fluorophore can already be detected with corresponding detectors even beneath the visual detection limit. Another advantage of fluorescent labeling is the possibility of the parallel measurement of fluorophores of different colors.

Especially suitable fluorophores are characterized by a strong absorption (a high extinction coefficient ε), a high quantum yield (Q>0.7) and a large Stokes shift. In the present case, TAMRA was selected as the color label for the displaceable ligand and the control compound, because it has a high extinction coefficient of 95,000 L cm$^{-1}$ mol$^{-1}$ and is also very conspicuously visible.

1.4 Supplying the Displaceable Ligand

Different small molecules and peptides were identified as displaceable ligands with the aid of the already described PAMP assay. The pyrogen E. coli LPS to be detected has a medium effective concentration (EC50) of 40 pg/mL in the PAMP assay with the NIH 3T3 pNifty SEAP TLR4/CD14 reporter cell line. So that LPS can displace a ligand bound to the receptor or the pyrogen binding domain thereof, it must have a lower binding affinity, which correlates with a lower EC50 value. Four peptides and two small molecules were identified as displaceable ligands with an agonistic effect with the aid of the PAMP assay:

Small molecule T5635346 (2-hydroxy-4-methylphenyl)-morpholin-4-ylmethanone); IC50 of 7.7 mM Small molecule T6854457 (4-methyl-N-(2-oxoazepan-3-yl)benzenesulfonamide); IC50 of 2.6 mM KGETVNTTISFSFKGIKFSK peptide (SEQ ID NO: 1);
IC50 > 200 mM KMQYPISINVNPCIELKGSK peptide (SEQ ID NO: 2);
IC50 > 200 mM GLLHIFYIPRRDLKQLYFNL peptide (SEQ ID NO: 3);
IC50 > 200 mM KRKEVICRGSDDDYSFCRAL peptide (SEQ ID NO: 4);
IC50 > 200 mM The affinity of a ligand to its receptor describes the tendency thereof to enter into a bond with the receptor. The greater affinity, the greater the association constant $K_a$ is. The strength of the receptor/ligand interaction can be determined experimentally with the aid of surface plasmon resonance spectroscopy (Biacore T200, GE Healthcare) and quantified by the so-called dissociation constant ($K_d$). $K_d$ is thereby the reciprocal value of $K_a$, a thermodynamic value, which indicates which portion of the ligand is bound on average to the receptor protein and has the dimension of a concentration. The Biacore chip system is based on a glass slide with a gold film in a flow cell. TLR4 was immobilized on the NTA sensor chip via its his-tag in accordance with the manufacturer's protocol and the to-be-tested ligands, control compounds and LPS were passed over it dissolved in HBS-P+ with 50 μM EDTA at 20° C. with a flow rate of 10 μL/min in respectively 5 concentrations. The bond with TLR4 is measured as a change in the refractive index in the flow cell as compared to a reference cell as a response difference in RU. 1 RU corresponds thereby to 1 pg of bound ligand. After ligand injection, buffer is used for rinsing in order to ideally recreate the initial state, complete disassociation of the ligand.

Table 2 lists the binding properties, determined with the aid surface plasmon resonance spectroscopy, of the small molecule T5635346 with and without TAMRA labeling as well as of LPS of Salmonella minnesota labeled with Alexa Fluor 488. T5635346 has an affinity for TLR4 in the same order of magnitude as the LPS tested here. However, the binding affinity is reduced by 40 fold by the TAMRA labeling.

TABLE 2

Binding properties of the small molecule T5635346 to TLR4

| Ligand | Mean Value in g/mol | $K_d$ in M | $K_a$ in 1/M |
|---|---|---|---|
| T5635346 | 221 | 2.42E−07 | 4,135,649 |
| T5635346-TAMRA | 723 | 8.50E−06 | 117,633 |
| LPS S. minnesota Alexa Fluor 488 | | 2.83E−07 | 4,203,447 |

1.5 Supplying the Control Compound

Analogous to identifying the displaceable ligands, small molecules and peptides not binding to the receptor also were identified as control compounds:

Small molecule T5874283 (1-(1,3-benzodioxol-5-yl)-3-[[4-(2-methylpropyl)morpholin-2-yl]methyl]urea)

Small molecule T7054880 (1-[1-(3-methoxyphenyl)propan-2-yl]-3-(1H-pyrazol-4-yl)urea)

FMMLGGLVRI peptide (SEQ ID NO: 5)

RMMWFGIMV peptide (SEQ ID NO: 6)

SGSPEEMLFCLEFVILHQPNSN peptide (SEQ ID NO: 7)

Surface plasmon resonance spectroscopy (see Section 1.4) was used to verify that the small molecules T7054880 and T5874283 selected as control compounds do not bind to TLR4 or bind to TLR4 with a similar affinity as LPS (see Table 3).

TABLE 3

Binding properties of the control compounds to TLR4

| Ligand | Mean Value in g/mol | $K_d$ in M | $K_a$ in 1/M |
|---|---|---|---|
| T5874283 | 335 | 1.02E−07 | 9,803,922 |
| T7054880 | 274 | — | — |

1.6 Immobilizing the Receptor on the Substrate

Figure 8:
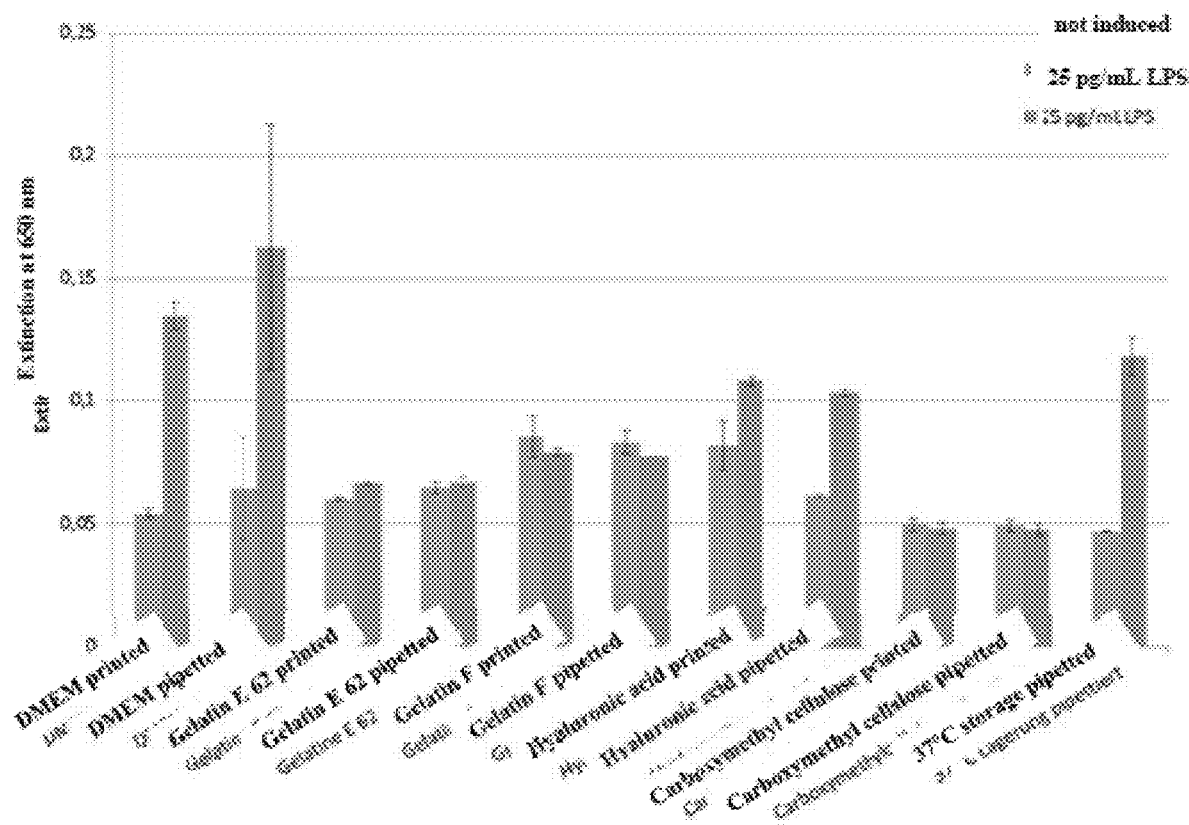
FIG. 8 shows the investigation of various printing inks. To this end, cells from the NIH 3T3 pNifty SEAP TLR4/CD14 reporter cell line were printed in different printing inks on the substrate or pipetted manually and then a PAMP assay was conducted to test the functionality of the receptors. 25 ng/mL of LPS served as a positive control, and n.i. is the non-induced negative control. The substrate turnover (Quanti-Blue™, InvivoGen) of the SEAP formed in the supernatant was [analyzed] after 30 min at a wavelength of l=650 nm.

In addition to immobilizing isolated receptors (see Section 1.2), cells from the reporter cell line were also printed on the Immunopore FP nitrocellulose membrane with the aid of a table-top robot mta TR300 printer (mta automation Inc.). First of all, suitable cell-compatible printing inks, such as e.g., inks based on hyaluronic acid (Lifecore Biomedicals), gelatin (Gelita AG) and carboxymethyl cellulose (Sigma-Aldrich GmbH) were tested for this. To this end, 100 µl with an absolute cell count of 30,000 cells was respectively printed at a speed of 15 µL/s per well of a 96-well microtiter plate or pipetted manually as a print control and the cells were incubated overnight at 37° C. On the second day, the cells were induced with 25 ng/mL of LPS and on the third day the secreted alkaline phosphatase in the supernatant was detected by the turnover of the Quanti-Blue™ substrate (InvivoGen) (FIG. 8).

Based on the comparison of the cells printed in DMEM and the cells pipetted manually it was shown that the printing process had only a small impact on the cells as compared to pipetting manually. Of the printing media tested, a printing ink of 1% hyaluronic acid dissolved in DMEM medium was identified as suitable and used for the following experiments.

Figure 9:
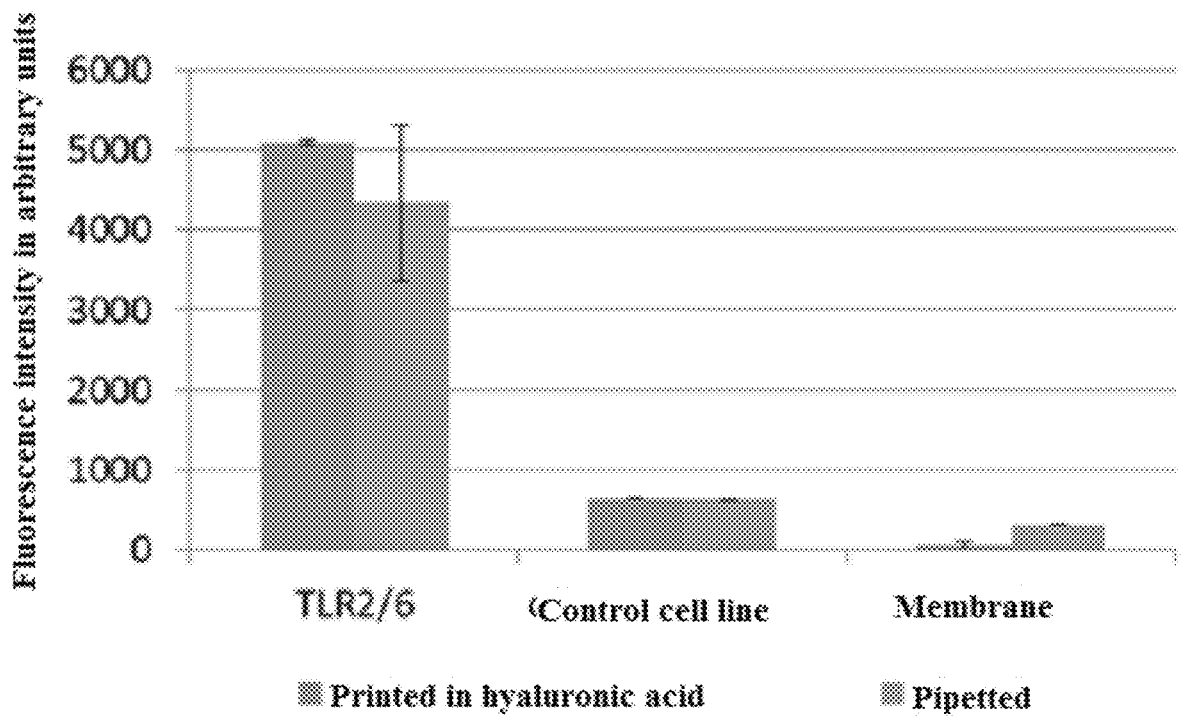
FIG. 9 shows the fluorescence intensities of pyrogens bound to printed cells. NIH 3T3 pNifty SEAP TLR2/6 cells and corresponding reporter cells without receptors were printed on Immunopore membranes in a hyaluronic acid printing ink. The pyrogen binding of rhodamine-labeled Pam3CSK4 was measured with fluorescence photometry at $l_{ex}$=549 nm and $l_{em}$=566 nm. The cells were also pipetted manually on the membrane to check the printing process.

To immobilize whole-cell reporter cells on membranes, NIH 3T3 pNifty SEAP TLR2/6 was printed on the Immunopore nitrocellulose membrane as an alternative to TLR4 expressed cells. A corresponding reporter cell line without TLR4 was also used to check a non-specific binding of the pyrogen. To this end, every four points was each printed with 40,000 cells for each test condition at a speed of 15 µLs on the Immunopore FP nitrocellulose membrane (1.5 cm×1.5 cm). As a control, 40,000 cells in 100 µL medium were pipetted manually in every four clone rings placed on the membrane in order to allow them to adhere in a stationary manner and to guarantee that the print pattern had similar test conditions for analysis. After incubation overnight at 37° C., on the following day, the Pam3CSK4 pyrogen with rhodamine labeling (6 ng/mL, Invivogen) that is specific for NIH 3T3 pNifty SEAP TLR2/6 was added and incubated at for 4 hours 37° C. to bind to the receptor. Prior to the fluorescence photometric measurement of the bound Pam3CSK4 with rhodamine labeling [at] $l_{ex}$=549 nm and $l_{em}$=566 nm, the individual samples were washed with PBS in order to remove non-bound pyrogen. FIG. 9 shows the results of the test described above for immobilizing the whole-cell reporter cells on membranes by means of printing methods. The vitality of the printed cells was of subordinate relevance for this test set-up. The main focus was that the membrane receptors were not damaged during the printing process and continued to have the ability for pyrogen binding. It was shown that by immobilizing by means of the printing methods, the membrane receptors are not damaged in direct comparison to the manually pipetted cells. In addition, it was shown that no undesired non-specific bonds occur between the pyrogen and membrane or the pyrogen and printing medium. Therefore, the printing offers the advantage that whole-cell sensor elements can be precisely positioned on a substrate in a spatially resolved manner.

In addition to the structure of a test strip, the storage suitability thereof must also be considered. If whole-cell sensor elements, i.e., receptor cells, are applied to a surface without a protective layer, there is a risk that membrane receptors will get damaged when transferring the cells to a storable state and lose their functionality. Printing the cells may also be a solution for this problem, because the cells are deposited here in a gel-like printing ink, which protects the cells from external influences. For this purpose, whole-cell sensor elements were printed as described above and pipetted manually as a control. Appropriate samples were subjected to three different preservation and storage methods: Drying at 37° C. for 24 hours, fixing with 70% ethanol and storage at 4° C. for 96 hours. After preservation and storage, the bond of the specific pyrogen Pam3CSK4 with rhodamine labeling was tested as already described above.

Figure 10A:
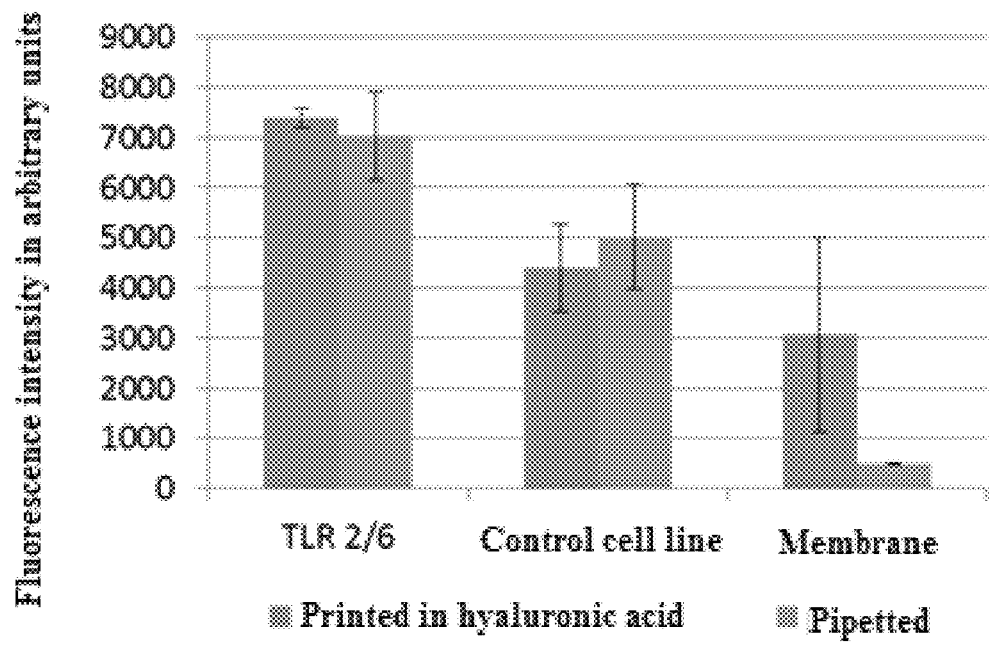
FIGS. 10A-10C show the fluorescence intensities of pyrogens bound to printed and preserved cells. NIH 3T3 pNifty SEAP TLR2/6 cells and corresponding reporter cells without receptors were printed on Immunopore membranes in a hyaluronic acid printing ink and preserved in different ways. The pyrogen binding of rhodamine-labeled Pam3CSK4 was measured with fluorescence photometry at $l_{ex}$=549 nm and $l_{em}$=566 nm. The cells were also pipetted manually on the membrane to check the printing process. Preservation methods.
Figure 10B:
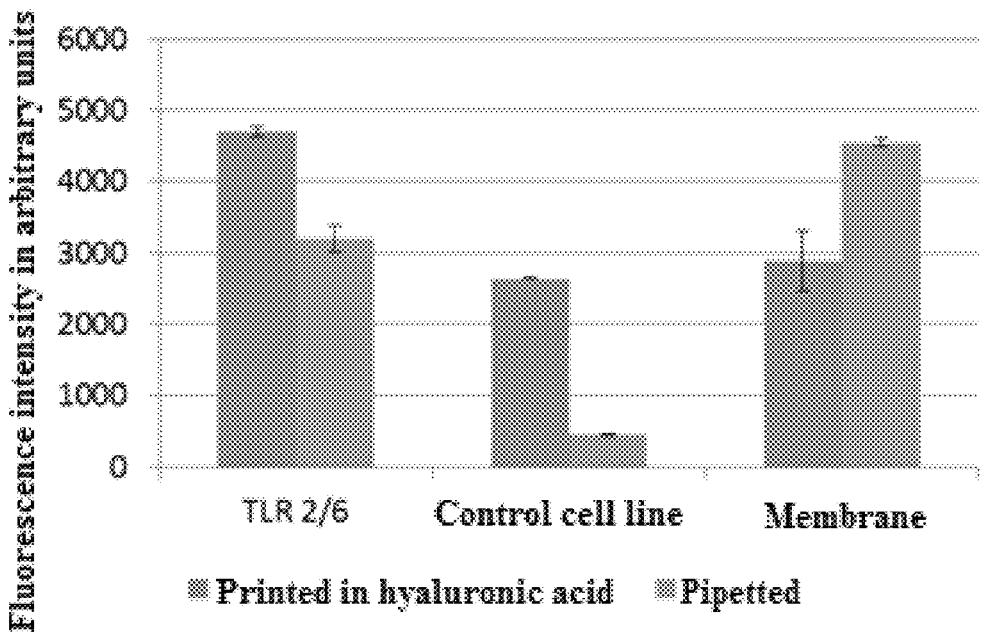
Figure 10C:
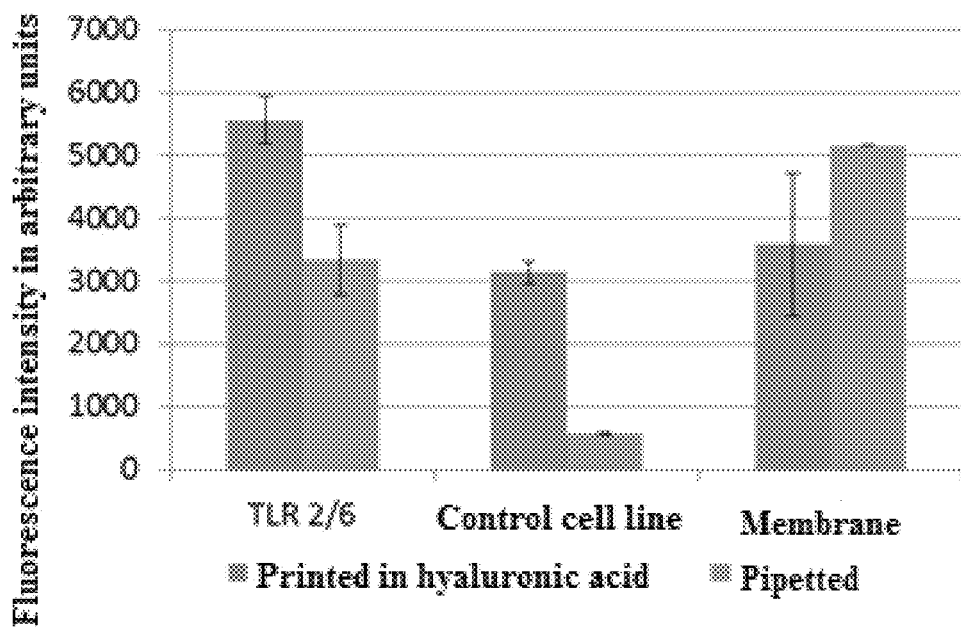

FIG. 10 shows the results of these investigations. As compared to the results in FIG. 9, higher values for the pyrogen binding to the control cell line and the membrane were always detected. It is a non-specifically bound pyrogen in this case. Roti® Block can be used for blocking to reduce the non-specific pyrogen binding to the membrane. FIG. 10A shows the results after drying, FIG. 10B the results of the ethanol fixing and FIG. 10C the results after storage at 4° C. With a high background from non-specific pyrogen binding to the membrane and control cell line, a clear delta of the fluorescence intensity of more than 3000 a.u. (arbitrary units) was detected nevertheless in the case of all preservation and storage methods. The comparison of printed receptors cells to receptor cells pipetted manually, which are not embedded in a gel-like protective matric, showed that the surrounding protective layer prevents a loss of function of the TLRs with storage and preservation.

1.7 Antibodies as Specific Ligand Capture Proteins

Specific capture proteins bind the displaceable ligand or the control compound in a spatially resolved manner. Antibodies in particular are suitable for this. They may be aimed either specifically at the displaceable ligand or the control compound or specifically against the fluorophore, which was used for the color labeling of the molecules. In Section 1.3, the fluorescence dyes, tetramethylrhodamine 5-carboxamido-(6-azidohexanyl) (TAMRA) and Alexa Fluor 488 were identified as suitable for labeling control compounds and displaceable ligands. Specific antibodies against these fluorophores are commercially available so that individual antibody production for selected displaceable ligands or control compounds may be dispensed with as the case may be, if the color properties of the fluorophore do not get lost when binding to the antigen.

The effect of the antibody binding on the fluorophores, Alexa Fluor 488 and TAMRA, was investigated by means of a specific dot blot. For this purpose, two different concentrations of the dyes (100 and 500 ng for Alexa Fluor 488 as well as 7 and 35 ng for TAMRA) were dotted on a nitrocellulose membrane and incubated further with the specific antibodies. The binding of the antibodies to the respective fluorophore was immunodetected by the horseradish peroxidase conjugated on the antibodies. In the case of both fluorophores, it was shown with the aid of fluorescence microscopy that the antibodies bind specifically to their respective antigen and they thereby do not show any declines in the fluorescence intensity. As a result, the selected anti-TAMRA and anti-Alexa Fluor 488 antibodies are suitable as capture proteins for the structure of the immunoassay test system.

1.8 Displaceable Ligand Receptor Complex

The central assay element of the immunoassay test system consists of the displaceable ligand receptor complex. It is cleaved by the presence of pyrogens, whereby the pyrogen displaces the displaceable ligand, binds to the receptor and the displaceable ligand is released. This was shown with the aid of Ni-NTA Magnetic Agarose Beads (Qiagen), bound on the TLR4 (Hölzel Diagnostik GmbH) by means of a his-tag (see FIG. 11).

Figure 11:
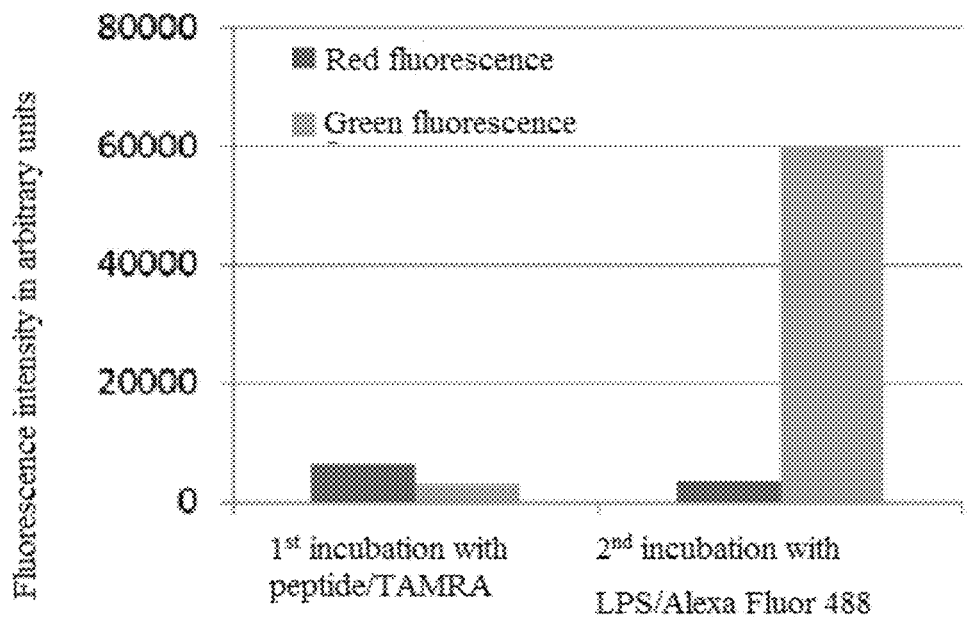
FIG. 11 shows the displacement of a displaceable ligand by LPS. To begin with, the TAMRA-labeled GLLHIFY-IPRRDLKQLYFNL peptide was bound as the displaceable ligand to TLR4 ($1^{st}$ incubation) on Ni-NTA Magnetic Agarose Beads (Qiagen), on which TLR4 was immobilized via the his-tag. In the subsequent second incubation, bound peptide was displaced by Alexa Fluor 488-labeled LPS. The displacement was tracked using fluorescence microscopy and fluorescence photometric analysis ($2^{nd}$ incubation).

In a first step, magnetic agarose beads loaded with TLR4 were incubated with TAMRA-labeled GLLHIFY-IPRRDLKQLYFNL peptide or with TAMRA-labeled small molecule T5635346 as the displaceable ligand for 1 hour at room temperature in binding buffer (50 mM NaH2PO2*2H2O; 300 mM NaCl; 20 mM Imidazol, pH 8.0). Non-bound ligands were removed in a wash step. In a second step, the magnetic agarose beads were incubated with the TLR4-displaceable ligand complex with Alexa Fluor 488-labeled *Salmonella minnesota* LPS in interaction buffer (binding buffer+0.05% Tween20). Non-bound ligands and any displaced ligands were removed in a subsequent wash step. Fluorescence images of the magnetic agarose beads were made after each incubation step. After the first incubation step, e.g., the binding of the peptide, i.e., of the displaceable ligand, is detectable as red dye on the bead surface via the TAMRA labeling. After the second incubation step, the displacement and release of the previously bound peptide is detectable as green dye on the bead surface through the binding of LPS via Alexa Fluor 488 labeling. FIG. 11 shows the associated fluorescence photometric analysis. The measured fluorescence of TAMRA drops from the first to the second incubation. This means that the TAMRA-labeled ligand was displaced. At the same time, however, the fluorescence of Alexa Fluor 488 increases from the first to the second incubation. This in turn means that the Alexa Fluor 488-labeled pyrogen LPS has occupied the previous binding sites of the TAMRA-labeled displaceable ligand.

The invention claimed is:

1. A competitive immunoassay test system for detecting at least one pyrogen contained in a liquid sample, the test system comprising:
   an assay carrier having:
      at least one immobilized pyrogen binding domain of at least one pattern recognition receptor (PRR) with at least one displaceable ligand comprising a first label,
      at least one immobilized ligand capture protein configured to bind the at least one displaceable ligand when it is displaced from the at least one immobilized pyrogen binding domain, and optionally
      a control compound comprising a second label,
   wherein the at least one immobilized pyrogen binding domain is selected from the group consisting of the pyrogen binding domains of a toll-like receptor (TLR), a NOD-like receptor (NLR), a RIG-I-like receptor (RLR), a C-type lectin receptor (CLR), a cytosolic dsDNA-sensor (CDSS), a scavenger receptor, a mannose-binding lectin 2 (MBL-2) receptor, a glucan receptor and combinations thereof, and
   wherein the first label and the second label, when present, are the same or different, and are selected from the group consisting of fluorescent dyes, colored latex particles, soot particles, magnetic particles, quantum dots, colloidal selenium particles, gold nanoparticles, gold clusters, colloidal gold particles, enzymes, chemiluminescent compounds, streptavidin, avidin, and biotin,
   wherein the test system is configured so that binding of the at least one displaceable ligand to the at least one ligand capture protein, after displacement of the at least one displaceable ligand from the at least one pyrogen binding domain of the PRR by the at least one pyrogen contained in the liquid sample, is indicated by a color reaction of the first label.

2. The test system according to claim 1, wherein the assay carrier is a microtiter plate well, a reagent container, a test tube or a substrate capable of capillary flow.

3. The test system according to claim 2, wherein the substrate that is capable of capillary flow has the following areas in a direction of capillary flow each spaced apart from one another:
   a) a sample application area;
   b) a reaction area having the at least one immobilized pyrogen binding domain of at least one PRR with the at least one displaceable ligand; and
   c) an analysis area having the at least one immobilized ligand capture protein for binding the displaced labeled ligand.

4. The test system according to claim 3, further comprising:
   b') a control compound area having at least one adsorbed, labeled control compound that does not bind to the at least one pyrogen binding domain of the PRR or the at least one ligand capture protein; and
   d) a control area having at least one immobilized control compound capture protein for binding the at least one labeled control compound.

5. The test system according to claim 4, wherein the areas a), b), c) and d) are each spaced apart from one another and the areas b) and b') overlap each other or are spaced apart from each other.

6. The test system according to claim 1, wherein the first label and the second label, when present, are selected from the group consisting of fluorescein isothiocyanate (FITC), fluorescein, rhodamine, ATTO dyes, Texas Red, phycoerythrin derivatives, cyanine fluorescent dyes, horseradish peroxidase (HRP), alkaline phosphatase (AP), glucose oxidase (GOx), β-D-galactosidase (β-Gal), glucose 6-phosphate dehydrogenase (G6PD), acridinium ester, acridinium sulfonamide, and isoluminol.

7. The test system according claim 1, wherein the liquid sample is a clinical sample, a medical sample, a pharmaceutical sample, a food technology sample, or an environmental sample.

8. The test system according to claim 1, wherein the liquid sample is a clinical sample, and the clinical sample is of human or non-human animal origin.

9. The test system according claim 1, wherein the at least one immobilized pyrogen binding domain is the pyrogen binding domain of a toll-like receptor (TLR).

10. The test system according to claim 1, wherein the at least one immobilized pyrogen binding domain is the pyrogen binding domain of one or more toll-like receptors (TLRs) selected from the group consisting of TLR 1, TLR 2, TLR 3, TLR 4, TLR 5, TLR 6, TLR 7, TLR 8, TLR 9 and heterodimers thereof.

11. The test system according to claim 1, wherein the at least one pyrogen to be detected is at least one selected from the group consisting of bacterial lipoproteins, bacterial lipopeptides, bacterial peptidoglycans, bacterial lipoteichoic acids, zymosan of yeast, double-stranded virus RNA, bacterial lipopolysaccharides (LPS), bacterial flagellin, unmethylated bacterial or viral DNA containing CpG, single-strand virus RNA and human heat shock protein 60.

12. The test system according claim 1, wherein the at least one immobilized pyrogen binding domain comprises the pyrogen binding domain of TLR4 and lipopolysaccharides (LPS) contained in the liquid sample are detected.

13. A method for detecting at least one pyrogen contained in a liquid sample, the method comprising:
 i) providing a test system according to claim 1,
 ii) bringing the liquid sample into contact with the assay carrier of the test system; and
 iii) analyzing a color reaction provided by the first label of the at least one displaceable ligand when the liquid sample comprises a pyrogen that displaces the at least one displaceable ligand from the at least one pyrogen binding domain, and the at least one displaceable ligand binds to the at least one ligand capture protein.

14. The method according to claim 13, wherein the assay carrier is a substrate capable of capillary flow and the liquid sample is applied to a sample application area in step ii) and conditions are provided and maintained for producing capillary flow from the sample application area to an analysis area of the substrate or to a control area of the substrate.

15. The method according to claim 14, wherein a pyrogen contained in the liquid sample is transported by capillary flow from the sample application area to a reaction area, where the pyrogen binds to the at least one immobilized pyrogen binding domain of the PRR and displaces the at least one displaceable ligand comprising the first label from the at least one immobilized pyrogen binding domain, and wherein the at least one displaceable ligand is transported to the analysis area where it binds to the at least one immobilized ligand capture protein and is detected by the color reaction of the first label.

16. The method according to claim 15, wherein the control compound is adsorbed in a control compound area and is transported by the capillary flow to the control area where the control compound binds to at least one immobilized control compound capture protein and is detected.

17. A competitive immunoassay test system for detecting at least one pyrogen contained in a liquid sample by analysis of a color reaction, the test system comprising:
 an assay carrier having:
  at least one immobilized pyrogen binding domain of at least one pattern recognition receptor (PRR) with at least one displaceable ligand comprising a first label,
  at least one immobilized ligand capture protein configured to bind the at least one displaceable ligand when it is displaced from the at least one immobilized pyrogen binding domain, and
  a control compound comprising a second label,
  wherein the first label and the second label, when present, are the same or different, and are selected from the group consisting of fluorescent dyes, colored latex particles, soot particles, magnetic particles, quantum dots, colloidal selenium particles, gold nanoparticles, gold clusters, colloidal gold particles, enzymes, chemiluminescent compounds, streptavidin, avidin, and biotin,
 wherein the test system is configured so that binding of the at least one displaceable ligand to the at least one ligand capture protein, after displacement of the at least one displaceable ligand from the at least one pyrogen binding domain of the PRR by the at least one pyrogen contained in the sample, is indicated by a color reaction of the label resulting from a contact of the liquid sample with the assay carrier.

18. A competitive immunoassay test system for detecting at least one pyrogen contained in a liquid sample, the test system comprising:
 an assay carrier having:
  at least one immobilized pyrogen binding domain of at least one pattern recognition receptor (PRR) with at least one displaceable ligand comprising a first label,
  at least one immobilized ligand capture protein configured to bind the at least one displaceable ligand when it is displaced from the at least one immobilized pyrogen binding domain, and optionally
  a control compound comprising a second label,
  wherein the first label and the second label, when present, are the same or different, and are selected from the group consisting of fluorescent dyes, colored latex particles, soot particles, magnetic particles, quantum dots, colloidal selenium particles, gold nanoparticles, gold clusters, colloidal gold particles, enzymes, chemiluminescent compounds, streptavidin, avidin, and biotin,
 wherein the test system is configured so that displacement of the at least one displaceable ligand from the at least one pyrogen binding domain by the at least one pyrogen contained in the liquid sample is indicated by a color reaction of the label.

19. The test system according claim 18, wherein the at least one immobilized pyrogen binding domain comprises a pyrogen binding domain of a toll-like receptor (TLR) and a pyrogen binding domain of a PRR selected from the group consisting of a NOD-like receptor (NLR), a RIG-I-like receptor (RLR), a C-type lectin receptor (CLR), a cytosolic dsDNA sensor (CDSS), a scavenger receptor, a mannose-binding lectin 2 (MBL-2) receptor, a glucan receptor, and combinations thereof.

20. The test system according to claim 18, wherein the at least one immobilized pyrogen binding domain comprises at least one of toll-like receptor (TLR) 4 or TLR 9.

* * * * *